United States Patent
Iriyama et al.

(10) Patent No.: US 11,564,959 B2
(45) Date of Patent: Jan. 31, 2023

(54) SCREENING METHOD FOR LAMININ 511 PRODUCTION PROMOTING AGENT, BASAL EPIDERMAL LAYER STABILIZING AGENT, AND/OR EPIDERMAL STEM CELLS REDUCTION INHIBITING OR PROLIFERATION PROMOTING AGENT

(71) Applicant: SHISEIDO COMPANY, LTD., Tokyo (JP)

(72) Inventors: Shunsuke Iriyama, Yokohama (JP); Saori Tanno, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 845 days.

(21) Appl. No.: 16/343,749

(22) PCT Filed: Oct. 20, 2017

(86) PCT No.: PCT/JP2017/038079
§ 371 (c)(1),
(2) Date: Apr. 19, 2019

(87) PCT Pub. No.: WO2018/074606
PCT Pub. Date: Apr. 26, 2018

(65) Prior Publication Data
US 2019/0275094 A1 Sep. 12, 2019

(30) Foreign Application Priority Data

Oct. 21, 2016 (JP) .............. JP2016-207027

(51) Int. Cl.
*A61K 36/03* (2006.01)
*A61P 29/00* (2006.01)
*C12N 9/24* (2006.01)
*C12N 9/50* (2006.01)
*G01N 33/50* (2006.01)
*A61P 43/00* (2006.01)
*A61K 31/4166* (2006.01)
*A61P 17/00* (2006.01)
*A61K 36/04* (2006.01)
*A61K 36/05* (2006.01)
*C12N 15/09* (2006.01)
*G01N 33/68* (2006.01)
*C12Q 1/68* (2018.01)

(52) U.S. Cl.
CPC .......... *A61K 36/03* (2013.01); *A61K 31/4166* (2013.01); *A61K 36/04* (2013.01); *A61K 36/05* (2013.01); *A61P 17/00* (2018.01); *A61P 29/00* (2018.01); *A61P 43/00* (2018.01); *C12N 9/2402* (2013.01); *C12N 9/50* (2013.01); *C12N 15/09* (2013.01); *C12Q 1/68* (2013.01); *G01N 33/5008* (2013.01); *G01N 33/68* (2013.01); *C12Y 302/01166* (2013.01); *C12Y 304/24035* (2013.01)

(58) Field of Classification Search
None
See application file for complete search history.

(56) References Cited

U.S. PATENT DOCUMENTS

| | | |
|---|---|---|
| 6,337,315 B1 | 1/2002 | Mahe et al. |
| 2012/0114690 A1 | 5/2012 | Ohishi et al. |
| 2012/0183481 A1 | 7/2012 | Iriyama et al. |

FOREIGN PATENT DOCUMENTS

| | | |
|---|---|---|
| DE | 27 46 650 A1 | 4/1979 |
| EP | 2 484 359 A1 | 8/2012 |
| JP | 2016-030750 A | 3/2016 |
| TW | 200914061 A | 4/2009 |
| WO | WO-2008/039515 A2 | 4/2008 |

OTHER PUBLICATIONS

Morvan et al., "Effects of Chlorella extract on skin" Personal Care 57-64 (Year: 2007).*
Suguwara et al., "Laminin-332 and -511 in skin" 17 Experimental Dermatology 473-480 (Year: 2008).*
Jaswir et al., "Anti-inflammatory compounds of macro algae origin: A review" 5(33) Journal of Medicinal Plants Research 7146-7154 (Year: 2011).*
Domogatskaya et al., "Laminin-511 but Not -332, -111, or -411 Enables Mouse Embryonic Stem Cell Self-Renewal In Vitro" 26 Stem Cells 2800-2809 (Year: 2008).*
Giangreco et al., "Human skin aging is Associated with Reduced Expression of the Stem Cell Markers β1 Integrin and MCSP," J. Invest. Dermatol., 2010, 130(2):604-608.
Imanishi et al., "Spatial and temporal control of laminin-332 and -511 expressions during hair morphogenesis," Med. Mol. Morphol., 2014, 47:38-42.
Muffler et al., "A Stable Niche Supports Long-Term Maintenance of Human Epidermal Stem Cells in Organotypic Cultures," Stem Cells, 2008, 26:2506-2515.
Nakashima et al., "What Kind of Signaling Maintains Pluripotency and Viability in Human-Induced Pluripotent Stem Cells Cultured in Laminin-511 with Serum-Free Medium?", BioResearch Open Access, May 1, 2016, 5(1):84-93.
Paquet-Fifield et al., "A role for pericytes as microenviromental regulators of human skin tissue regeneration," Journal of Clinical Investigation, Jan. 1, 2009, 119(9):2795-2806.

* cited by examiner

*Primary Examiner* — Nancy J Leith
(74) *Attorney, Agent, or Firm* — Foley & Lardner LLP

(57) ABSTRACT

Provided is a screening method for a laminin 511 expression promoter, which takes the expression of laminin 511 as an indicator. Also provided is an agent for improving skin barrier function, elasticity, hydration and inflammation. This agent includes at least one extract selected from among a group consisting of brown algae, red algae and green algae.

4 Claims, 19 Drawing Sheets
Specification includes a Sequence Listing.

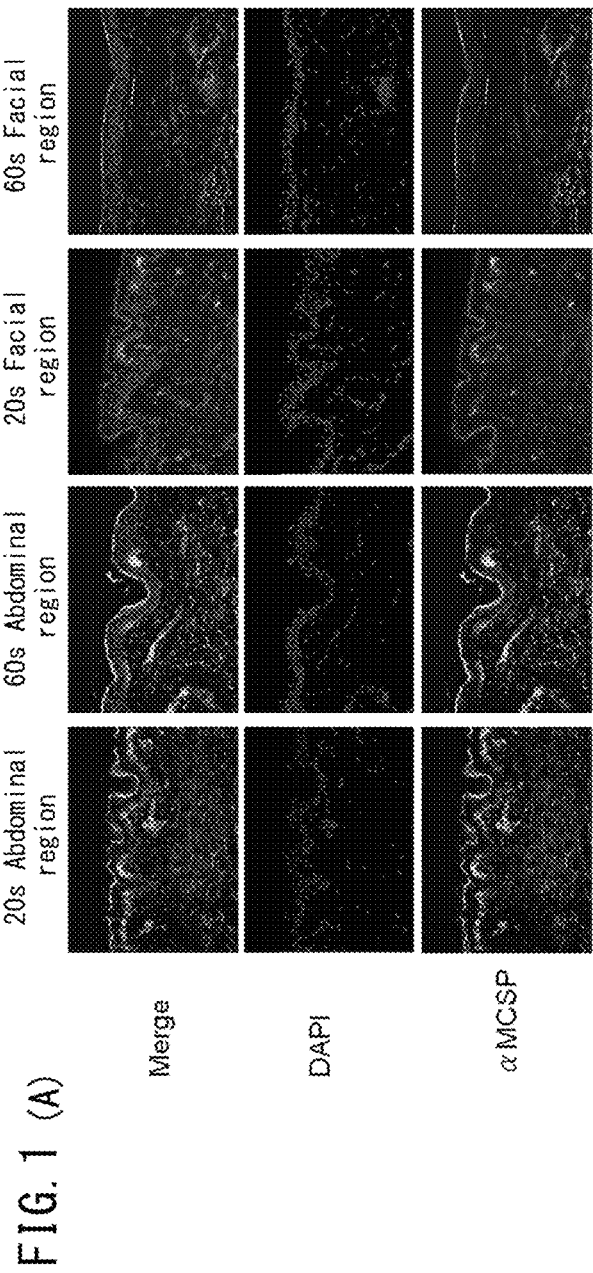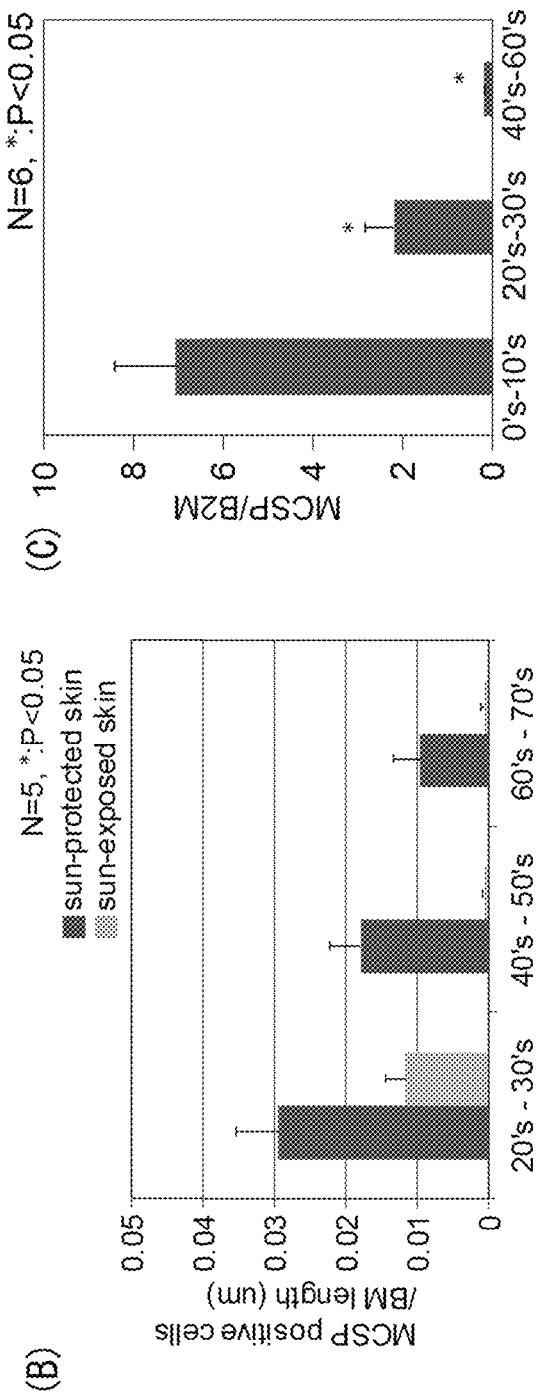
FIG. 1

FIG. 2
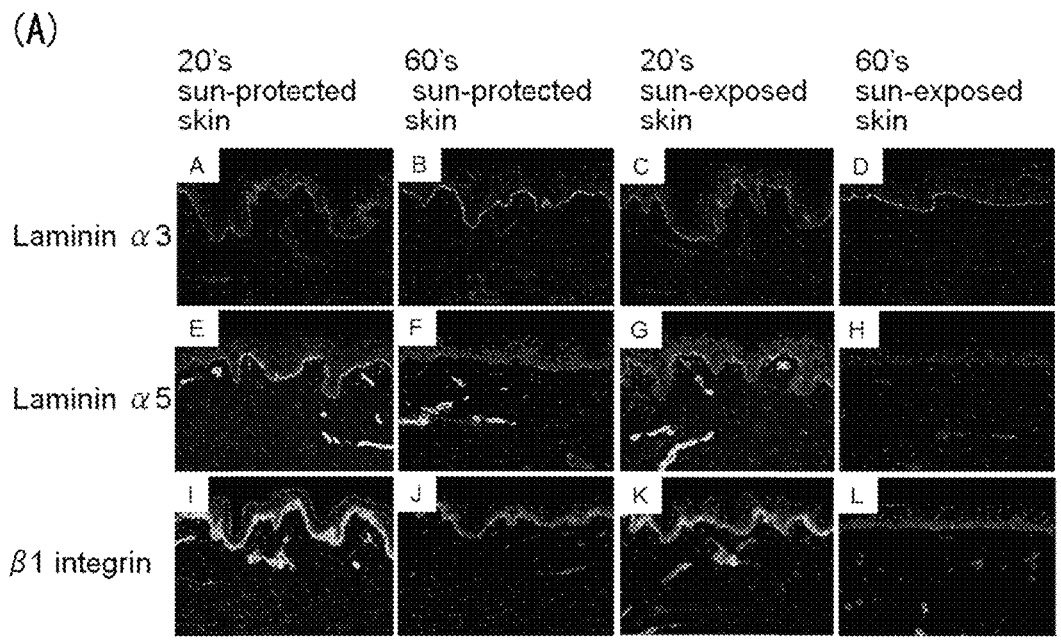
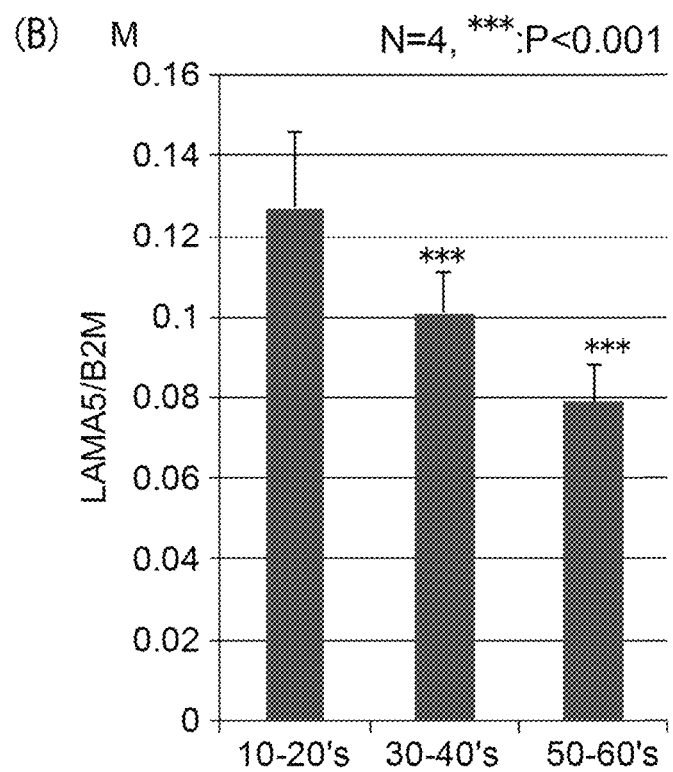

FIG. 3
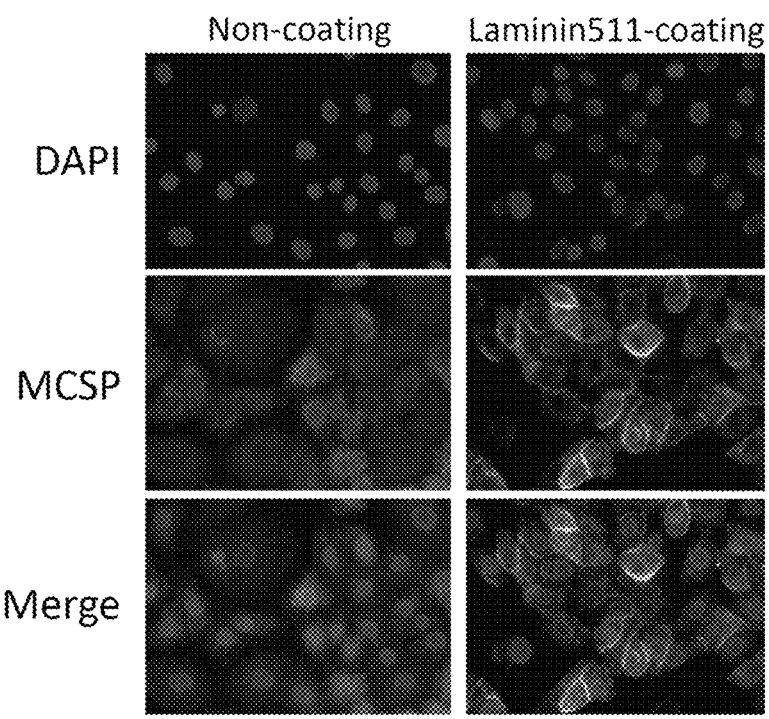
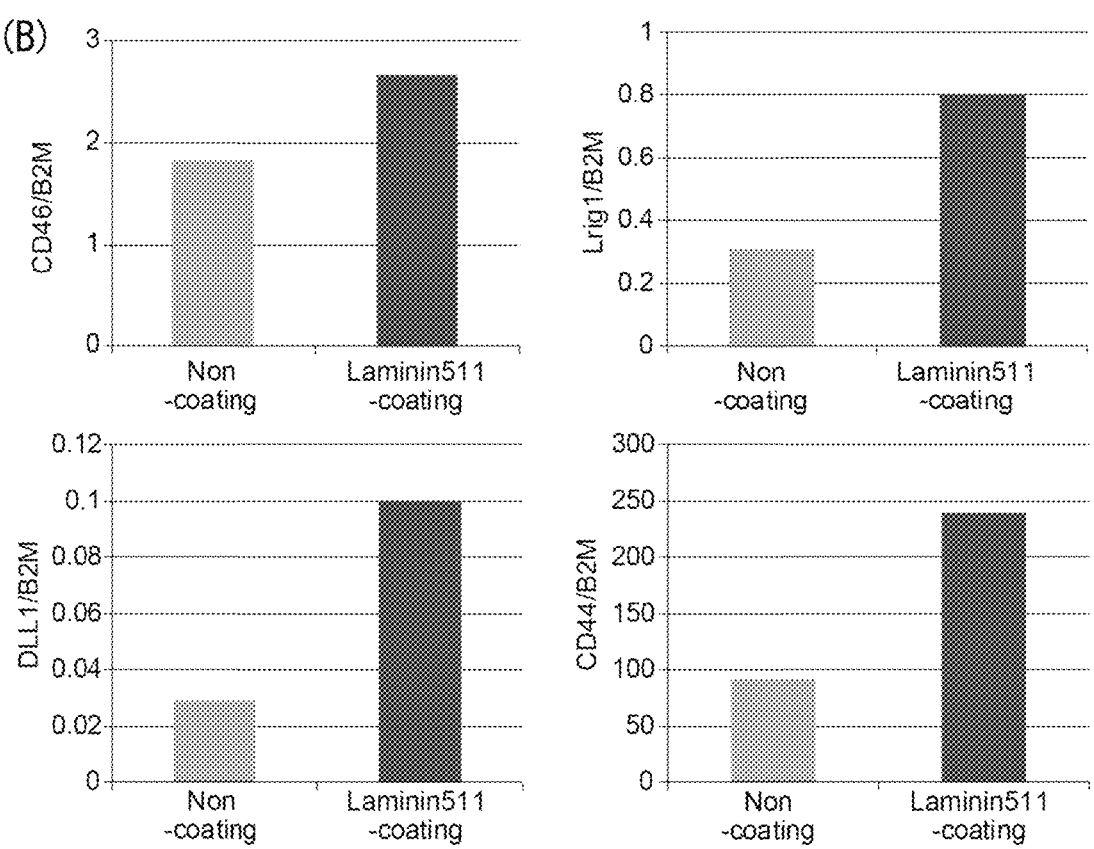

FIG. 5
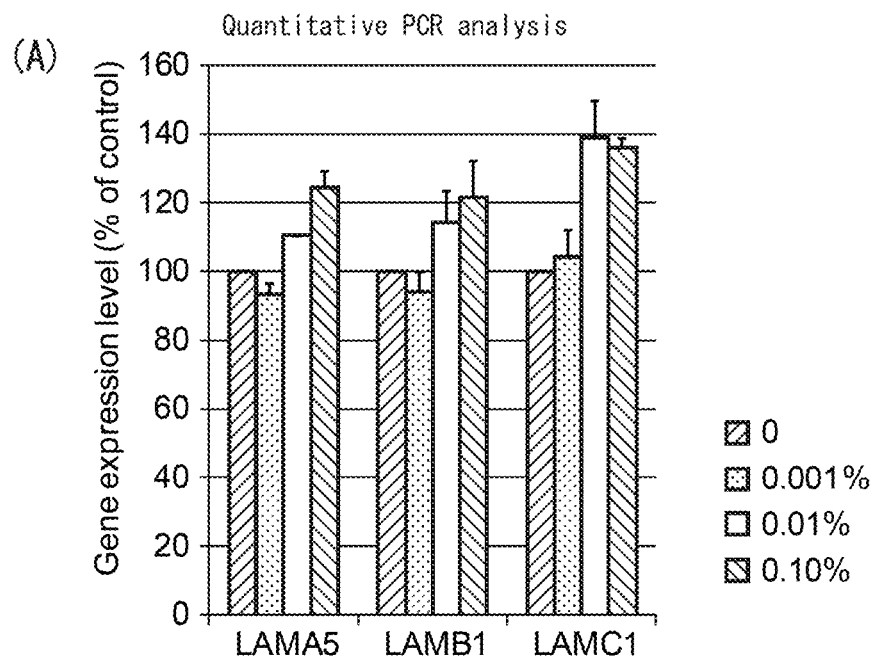
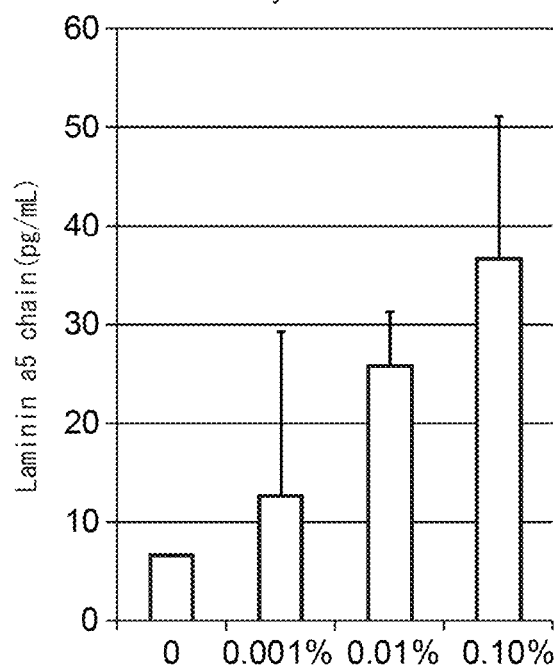

FIG. 10 (A)
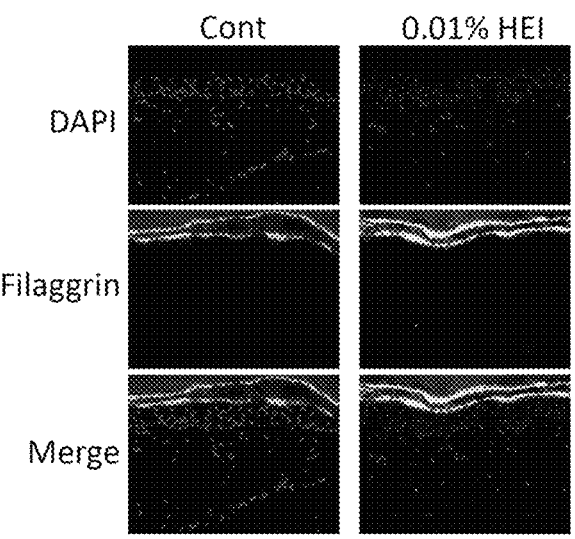
(B) 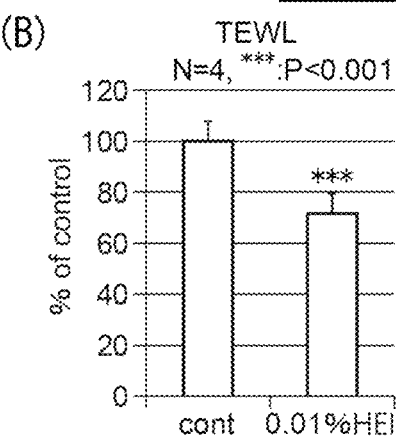
(C) 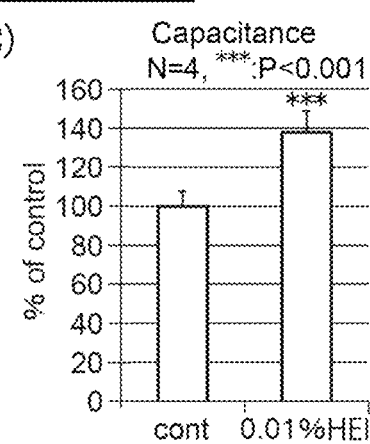
(D) 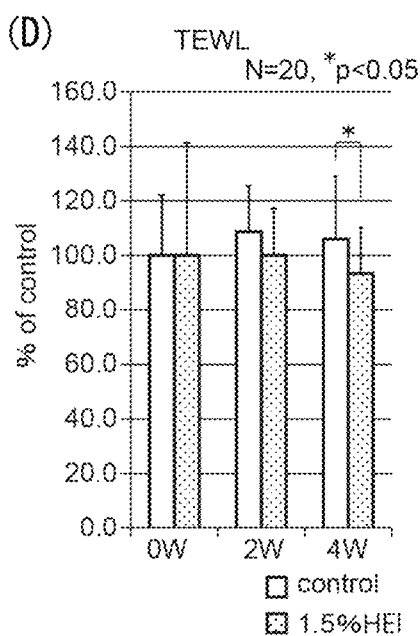
(E) 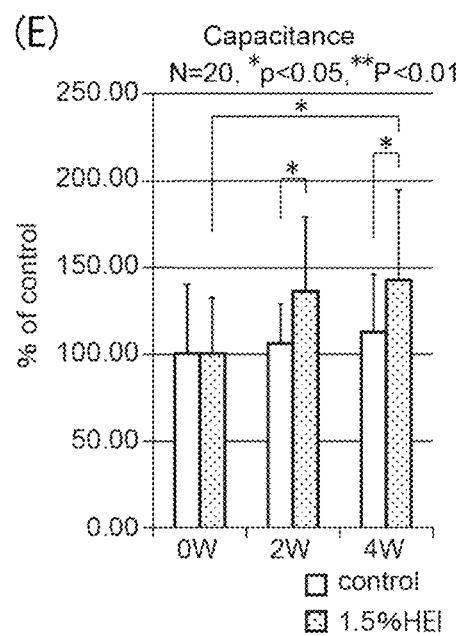

FIG. 11
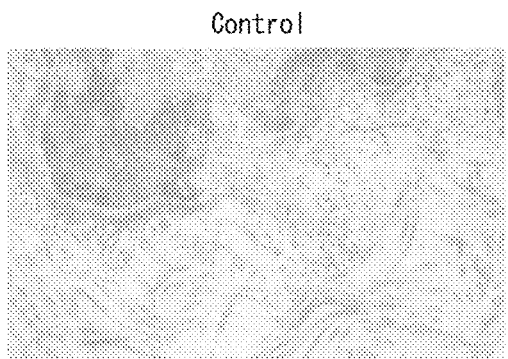
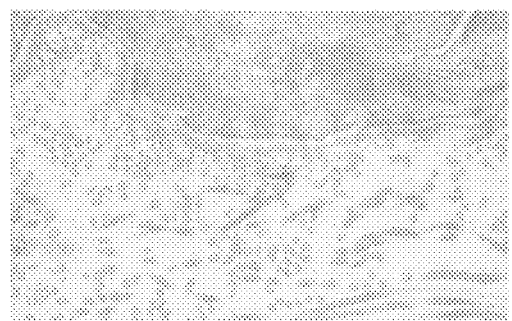
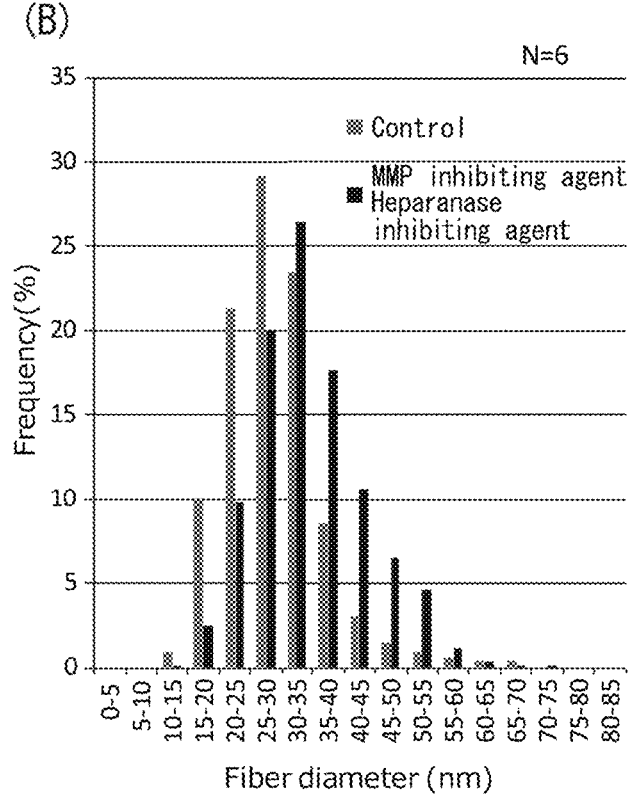
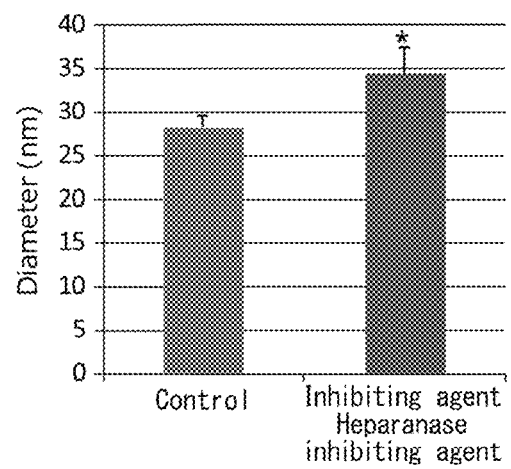
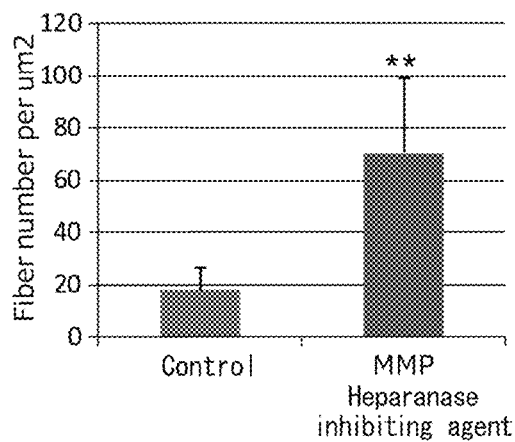

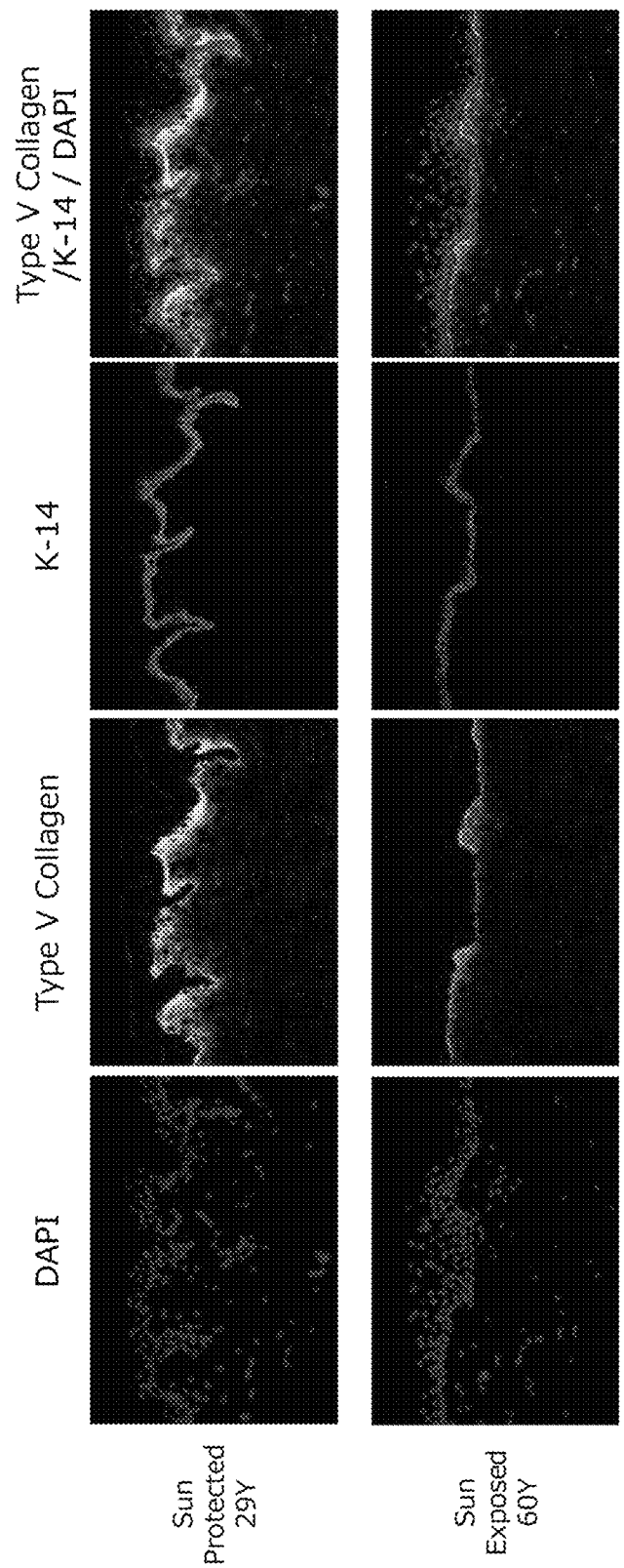

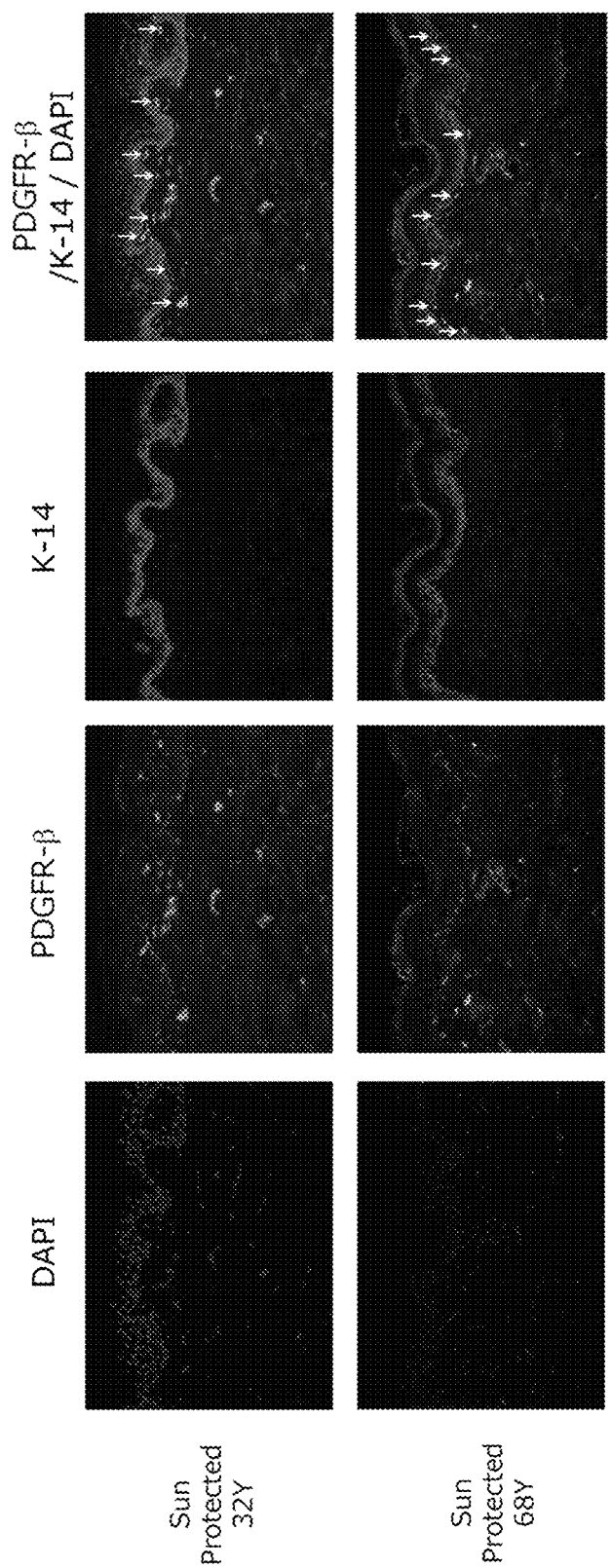

SEQUENCE LISTING

<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
cacggctctg accgacatag                20

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
cccagccctc tacgacagt                 19

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
gtgggatcga gacatgtaag ca             22

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
caatccaaat gcggcatct                                                    19

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
tggctggatt atgtactcgt gg                                                22

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
ctgtagcacc tacttcgtgg ca                                                22

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
ctttgtagtc tctggcaaga tgc                                               23

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
cgggtataaa cttcaactct gtgc                                              24

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tccaaggata tatgccccaa                                                   20

<210> SEQ ID NO 10
<211> LENGTH: 20
<212> TYPE: DNA
<213> ORGANISM: Artificial Sequence
<220> FEATURE:

```
<223> OTHER INFORMATION: Primer

<400> SEQUENCE: 10
gaactcggtt tctcagcagc                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cttgacctgg gttctgggta                                              20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ggccaaagga acatttgaag                                              20

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
ttgcagtcaa cagtcgaa                                                18

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
ttctgacgac tccttgttc                                               19

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
ttggaccaag atgtcctgag                                              20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
caatatattc tgcctccccg                                              20
```

```
<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gtgctgttgt tcccaagaca                                              20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
gccatcatca cagagctcac                                              20

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
cgcgtagtga tgccatgtaa ctgaa                                        25

<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
cgcttcgatc ccaagaagga atcaa                                        25

<210> SEQ ID NO 21
<211> LENGTH: 18
<212> TYPE: DNA
<213> ORGANISM: Artificial Sequence
<220> FEATURE:
<223> OTHER INFORMATION: Primer

<400> SEQUENCE: 21
cctggcatgc aagtgtga                                                18

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
cgaatggtca cccgagttt                                               19

<210> SEQ ID NO 23
<211> LENGTH: 19
<212> TYPE: DNA
<213> ORGANISM: Artificial Sequence
<220> FEATURE:
<223> OTHER INFORMATION: Primer
```

```
<400> SEQUENCE: 23
tcagagcact gggacgaag                                              19

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
cccaacacct ccaaccat                                               18

<210> SEQ ID NO 25
<211> LENGTH: 27
<212> TYPE: DNA
<213> ORGANISM: Artificial Sequence
<220> FEATURE:
<223> OTHER INFORMATION: Primer

<400> SEQUENCE: 25
gcacagggaa gtcacagatg tatgtgc                                     27

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
ccactggtca cgttcaggat gaag                                        24

<210> SEQ ID NO 27
<211> LENGTH: 25
<212> TYPE: DNA
<213> ORGANISM: Artificial Sequence
<220> FEATURE:
<223> OTHER INFORMATION: Primer

<400> SEQUENCE: 27
gggtacccag ttaaattttc atttc                                       25

<210> SEQ ID NO 28
<211> LENGTH: 26
<212> TYPE: DNA
<213> ORGANISM: Artificial Sequence
<220> FEATURE:
<223> OTHER INFORMATION: Primer

<400> SEQUENCE: 28
caagtttcaa ccagcaagaa attact                                      26

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
gtggcacaga attgctctca                                             20

<210> SEQ ID NO 30
<211> LENGTH: 20
```

```
<212> TYPE: DNA
<213> ORGANISM: Artificial Sequence
<220> FEATURE:
<223> OTHER INFORMATION: Primer

<400> SEQUENCE: 30
tcaccctcaa acacctcctc                                               20

<210> SEQ ID NO 31
<211> LENGTH: 19
<212> TYPE: DNA
<213> ORGANISM: Artificial Sequence
<220> FEATURE:
<223> OTHER INFORMATION: Primer

<400> SEQUENCE: 31
gaaggtgaag gtcggagtc                                                19

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
gaagatggtg atgggatttc                                               20

<210> SEQ ID NO 33
<211> LENGTH: 18
<212> TYPE: DNA
<213> ORGANISM: Artificial Sequence
<220> FEATURE:
<223> OTHER INFORMATION: Primer

<400> SEQUENCE: 33
cctggcatgc aagtgtga                                                 18

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
cgaatggtca cccgagttt                                                19

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
gtgggatcga gacatgtaag ca                                            22

<210> SEQ ID NO 36
<211> LENGTH: 19
<212> TYPE: DNA
<213> ORGANISM: Artificial Sequence
<220> FEATURE:
<223> OTHER INFORMATION: Primer
```

```
<400> SEQUENCE: 36
caatccaaat gcggcatct                                                 19
```

SCREENING METHOD FOR LAMININ 511 PRODUCTION PROMOTING AGENT, BASAL EPIDERMAL LAYER STABILIZING AGENT, AND/OR EPIDERMAL STEM CELLS REDUCTION INHIBITING OR PROLIFERATION PROMOTING AGENT

CROSS-REFERENCE TO RELATED APPLICATIONS

This application is a National Stage application of PCT/JP2017/038079, filed Oct. 20, 2017, which claims priority from Japanese application JP 2016-207027, filed Oct. 21, 2016.

The instant application contains a Sequence Listing which has been submitted in ASCII format via EFS-WEB and is hereby incorporated by reference in its entirety. Said ASCII copy, created on Apr. 19, 2019, is named sequence.txt and is 6,828 bytes.

FIELD

The present invention relates to the technical field of inhibiting reduction or promoting increase of epidermal stem cells in the epidermal basal membrane.

BACKGROUND

The epidermis is a skin tissue present on the outermost layer of skin. The epidermis is composed mainly of the stratum corneum, granular layer, stratum spinosum and basal lamina. Basal cells in the basal lamina divide and migrate to the outer layer. During the course of migration, these cells become enucleated and flattened to differentiate to the stratum corneum, and then the stratum corneum eventually sloughs off. The turnover period is said to last about 45 days. Senescent skin, however, has a slower turnover rate, such that the epidermis becomes thinner as a whole. This is known to result in loss of skin function, including reduced barrier function and lower moisture content. Basal cells are highly divisible but do not undergo unlimited repeated division, dividing a fixed number of times and then failing to divide further. Basal cells are newly supplied by differentiation of a subset of the epidermal basal stem cells residing on the basal membrane. However, the number of epidermal basal stem cells is known to decrease with senescence, and when the number of epidermal basal stem cells decreases, signs of aging appear such as thinning of the epidermis, drying of the epidermis and reduction in its barrier function.

MCSP antibodies have recently been developed as epidermal basal stem cell markers, and such antibodies can be used to identify epidermal basal stem cells. Visualization of epidermal basal cells using MCSP antibodies has been carried out in skin at unexposed sections of males and females of different age groups, and it has been demonstrated that the number of MCSP-positive epidermal basal stem cells decreases with age (NPL 1). There is a demand, therefore, to develop drugs that promote increase or inhibit reduction of the number of MCSP-positive epidermal basal stem cells.

CITATION LIST

Non Patent Literature

[NPL 1] Giangreco A, et al., J Invest Dermatol. 2010, 130(2): 604-8

SUMMARY

Technical Problem

It is an object of the present invention to provide a method for promoting increase or inhibiting reduction in the number of MCSP-positive epidermal basal stem cells.

Solution to Problem

As a result of avid research on MCSP-positive epidermal basal stem cells, the present inventors have found a relationship between MCSP-positive epidermal basal stem cells and laminin 511 present near the basal membrane. Specifically, it has been found for the first time that when laminin 511 near the basal membrane decreases, the number of MCSP-positive epidermal basal stem cells correspondingly decreases, and that by increasing the expression level of laminin 511 it is possible to increase the number of MCSP-positive epidermal basal stem cells. It has also been found that since laminin is a complex of laminin α, β and γ, the abundance of laminin 511 can be determined using expression levels of laminin α5, β1 and γ1 as the index.

Based on this knowledge, an invention was devised relating to a screening method for a laminin 511-expression promoting agent using expression of laminin 511 as the index. A laminin 511-expression promoting agent can stabilize the basal membrane, and therefore a screening method for a laminin 511-expression promoting agent may be considered to be a screening method for basal membrane stabilizing agents. Moreover, since increase in the presence of laminin 511 and stabilization of the basal membrane result in effects of increasing epidermal basal stem cells or inhibiting their reduction, a screening method for a laminin 511-expression promoting agent may also be considered to be a screening method for a promoting agent for increasing or an inhibiting agent for reducing epidermal basal stem cells.

More specifically, the present invention relates to the following.

[1] A screening method for a laminin 511-expression promoting agent, wherein the expression level of laminin 511 in epidermal cells is used as an index.

[2] The method according to [1], which comprises:
a step of culturing epidermal cells in a culture medium containing a candidate drug,
a step of measuring the expression level of laminin 511 in the epidermal cells, and
a step of judging the candidate drug to have an effect of promoting expression of laminin 511 when the expression level of laminin 511 has increased compared to a control expression level of laminin 511.

[3] The method according to [1] or [2], wherein the expression level of laminin 511 is determined from the protein level of laminin 511 or one or more mRNA levels selected from the group consisting of the mRNA level of laminin α5, the mRNA level of laminin β1 and the mRNA level of laminin γ1.

[4] The method according to any one of [1] to [3], wherein the expression level of laminin 511 is determined from the total amount of the mRNA level of laminin α5, the mRNA level of laminin β1 and the mRNA level of laminin γ1.

[5] The method according to any one of [1] to [4], wherein the laminin 511-expression promoting agent is an epidermal basal membrane stabilizing agent.

[6] The method according to any one of [1] to [5], wherein the epidermal basal membrane stabilizing agent is a reduction inhibiting agent or an proliferation promoting agent of epidermal basal stem cells.

[7] The method according to any one of [1] to [6], wherein the epidermal cells comprises epidermal stem cells.

[8] The method according to any one of [1] to [7], wherein the epidermal stem cells comprise epidermal basal stem cells.

[9] The method according to any one of [1] to [8], wherein the epidermal cells comprise MCSP-expressing cells.

[10] The method according to any one of [1] to [9], wherein the epidermal cells comprise cells that also express integrin.

[11] The method according to any one of [1] to [10], wherein the epidermal cells are derived from a fetus.

[12] A laminin 511 expression promoting agent, comprising at least one extract selected from the group consisting of brown algae, red algae and green algae, or 1-(2-hydroxyethyl)-2-imidazolidinone as an active ingredient.

[13] An epidermal basal membrane stabilizing agent that acts by promoting expression of laminin 511, comprising at least one extract selected from the group consisting of brown algae, red algae and green algae, or 1-(2-hydroxyethyl)-2-imidazolidinone as an active ingredient.

[14] A reduction inhibiting agent or an increasing agent of epidermal basal stem cells that acts by promoting expression of laminin 511, comprising at least one extract selected from the group consisting of brown algae, red algae and green algae, or 1-(2-hydroxyethyl)-2-imidazolidinone as an active ingredient.

[15] An extracellular matrix degrading enzyme activity inhibiting agent comprising 1-(2-hydroxyethyl)-2-imidazolidinone.

[16] The extracellular matrix degrading enzyme activity inhibiting agent according to [15], wherein the extracellular matrix degrading enzyme is a matrix metalloproteinase or a heparanase.

[17] The extracellular matrix degrading enzyme activity inhibiting agent according to [15], wherein the extracellular matrix degrading enzyme is matrix metalloproteinase 9.

[18] A laminin 511 degradation inhibiting agent comprising an extracellular matrix degrading enzyme activity inhibiting agent according to any one of [15] to [17].

[19] An epidermal basal membrane stabilizing agent comprising an extracellular matrix degrading enzyme activity inhibiting agent according to any one of [15] to [17].

[20] An epidermal basal stem cell reduction inhibiting or proliferation promoting agent comprising an extracellular matrix degrading enzyme activity inhibiting agent according to any one of [15] to [17].

[21] A method of promoting expression of laminin 511 in the epidermis, comprising administration of at least one extract selected from the group consisting of brown algae, red algae and green algae, or 1-(2-hydroxyethyl)-2-imidazolidinone.

[22] A method of stabilizing the epidermal basal membrane through an effect of promoting expression of laminin 511, comprising administration of at least one extract selected from the group consisting of brown algae, red algae and green algae, or 1-(2-hydroxyethyl)-2-imidazolidinone.

[23] A method of inhibiting reduction or promoting increase of epidermal basal stem cells through an effect of promoting expression of laminin 511, comprising administration of at least one extract selected from the group consisting of brown algae, red algae and green algae, or 1-(2-hydroxyethyl)-2-imidazolidinone, and producing.

[24] A cosmetic method comprising administration of at least one extract selected from the group consisting of brown algae, red algae and green algae, or 1-(2-hydroxyethyl)-2-imidazolidinone, thereby enhancing the expression of laminin 511 in the epidermis.

[25] A cosmetic method comprising administration of at least one extract selected from the group consisting of brown algae, red algae and green algae, or 1-(2-hydroxyethyl)-2-imidazolidinone, thereby enhancing expression of laminin 511 in the epidermis, wherein the epidermal basal membrane is stabilized by the effect of promoting expression of laminin 511.

[26] A cosmetic method comprising administration of at least one extract selected from the group consisting of brown algae, red algae and green algae, or 1-(2-hydroxyethyl)-2-imidazolidinone, thereby enhancing expression of laminin 511 in the epidermis, wherein the effect of promoting expression of laminin 511 inhibits reduction or promotes increase in epidermal basal stem cells.

[27] Use of at least one extract selected from the group consisting of brown algae, red algae and green algae, or 1-(2-hydroxyethyl)-2-imidazolidinone, for preparing a cosmetic or medicament for promoting expression of laminin 511.

[28] Use of at least one extract selected from the group consisting of brown algae, red algae and green algae, or 1-(2-hydroxyethyl)-2-imidazolidinone, for preparing a cosmetic or medicament for stabilizing the epidermal basal membrane.

[29] Use of at least one extract selected from the group consisting of brown algae, red algae and green algae, or 1-(2-hydroxyethyl)-2-imidazolidinone, for preparing a cosmetic or medicament for inhibiting reduction or promoting increase in epidermal basal stem cells.

[30] At least one extract selected from the group consisting of brown algae, red algae and green algae, or 1-(2-hydroxyethyl)-2-imidazolidinone for use in anti-aging treatment via promoting expression of laminin 511.

[31] At least one extract selected from the group consisting of brown algae, red algae and green algae, or 1-(2-hydroxyethyl)-2-imidazolidinone for use in anti-aging treatment via stabilizing the epidermal basal membrane.

[32] At least one extract selected from the group consisting of brown algae, red algae and green algae, or 1-(2-hydroxyethyl)-2-imidazolidinone, for use in anti-aging treatment via inhibiting decrease or promoting increase in epidermal basal stem cells.

[33] 1-(2-Hydroxyethyl)-2-imidazolidinone, for use in anti-aging treatment via inhibiting an activity of an extracellular matrix degrading enzyme.

[34] 1-(2-hydroxyethyl)-2-imidazolidinone according to [33], wherein the extracellular matrix degrading enzyme is a matrix metalloproteinase or heparanase.

[35] The 1-(2-hydroxyethyl)-2-imidazolidinone according to [33], wherein the extracellular matrix degrading enzyme is matrix metalloproteinase 9.

[36] An improving agent for skin barrier, elasticity, moisture or inflammation, comprising at least one extract selected from the group consisting of brown algae, red algae and green algae.

[37] A suppressing agent for inflammation, comprising at least one extract selected from the group consisting of brown algae, red algae and green algae.

[38] Use of at least one extract selected from the group consisting of brown algae, red algae and green algae, for preparing an improving agent for skin barrier, elasticity, moisture and inflammation.

[39] Use of at least one extract selected from the group consisting of brown algae, red algae and green algae for preparing a suppressing agent for inflammation.

[40] A cosmetic method for improving skin barrier, elasticity, moisture and inflammation, comprising applying a cosmetic including at least one extract selected from the group consisting of brown algae, red algae and green algae, to a subject in need of improvement in skin barrier, elasticity, moisture and inflammation.

[41] A cosmetic method for inhibiting inflammation, comprising applying a cosmetic including at least one extract selected from the group consisting of brown algae, red algae and green algae to a subject suffering from inflammation.

Advantageous Effects of Invention

Screening of drugs that increase MCSP-positive epidermal basal stem cells can be carried out by conducting more simple cell examination which uses laminin 511 as an index.

BRIEF DESCRIPTION OF DRAWINGS

FIG. 1A is set of photographs showing expression of MCSP in the abdominal region (unexposed section) and facial region (exposed section) of a person in their 20s, and in the abdominal region (unexposed section) and facial region (exposed section) of a person in their 60s. FIG. 1B is a graph showing comparison of the number of MCSP-positive cells measured per length of the basal membrane in skin slices of the abdominal region (unexposed section) and the facial region (exposed section) of subjects in different age groups. FIG. 1C is a graph showing comparison of expression levels of MCSP in skin slices from subjects in different age groups.

FIG. 2A is a set of photographs showing expression of laminin 332, laminin 551 and β1 integrin in the abdominal region (unexposed section) and facial region (exposed section) of a person in their 20s, and in the abdominal region (unexposed section) and facial region (exposed section) of a person in their 60s. FIG. 2B is a graph showing comparison of expression levels of laminin α5 in skin slices from subjects in different age groups.

FIG. 3A is a set of photographs showing the effects on MCSP expression when a culture plate has been coated with laminin 511 during culturing of skin. FIG. 3B is a set of graphs showing the effects on gene expression of stem cell markers consisting of CD46, Lrig1, DLL1 and CD44, when a culture plate has been coated with laminin 511 during culturing of skin.

FIG. 5A is a graph showing dose-dependent increase in gene expression of laminin α5, laminin β1 and laminin γ1 by addition of Algaerex. FIG. 5B is a graph showing dose-dependent increase in protein level of the laminin α5 chain by addition of Algaerex.

FIG. 10A is a set of photographs showing the effect on filaggrin protein expression by addition of 1-(2-hydroxyethyl)-2-imidazolidinone (HEI) in ex vivo human skin organ culturing. FIGS. 10B and C are graphs showing change in TEWL and stratum corneum moisture contents by addition of 1-(2-hydroxyethyl)-2-imidazolidinone (HEI) in ex vivo human skin organ culturing. FIGS. 10D and E are graphs showing change in TEWL and stratum corneum moisture contents by 1-(2-hydroxyethyl)-2-imidazolidinone (HEI) in an in vivo-single mask human application test.

FIG. 11A is a pair of electron micrographs of a region directly under the basal membrane, taken after addition of an MMP inhibiting agent (CGS27023A) and a heparanase inhibiting agent (BIPBIPU) in organ culturing of skin tissue. A cross-section of collagen fibers appears below the basal membrane. FIG. 11B is a histogram showing diameter and frequency of collagen fibers measured in the electron micrographs. FIG. 11C shows the mean values for the diameters of fibers in the electron micrographs. FIG. 11D is a graph showing the mean values for the density of fibers in the electron micrographs.

FIG. 12A is a set of fluorescent microscope photographs showing expression of type V collagen and expression of K-14, representing keratinocytes, in skin samples taken from a young subject (29 years of age) and an older subject (60 years of age).

FIG. 16A is a set of fluorescent microscope photographs showing expression of PDGFRβ and expression of K-14, representing keratinocytes, in skin sample taken from a young subject (32 years of age) and an older subject (68 years of age).

DESCRIPTION OF EMBODIMENTS

Figure 4:
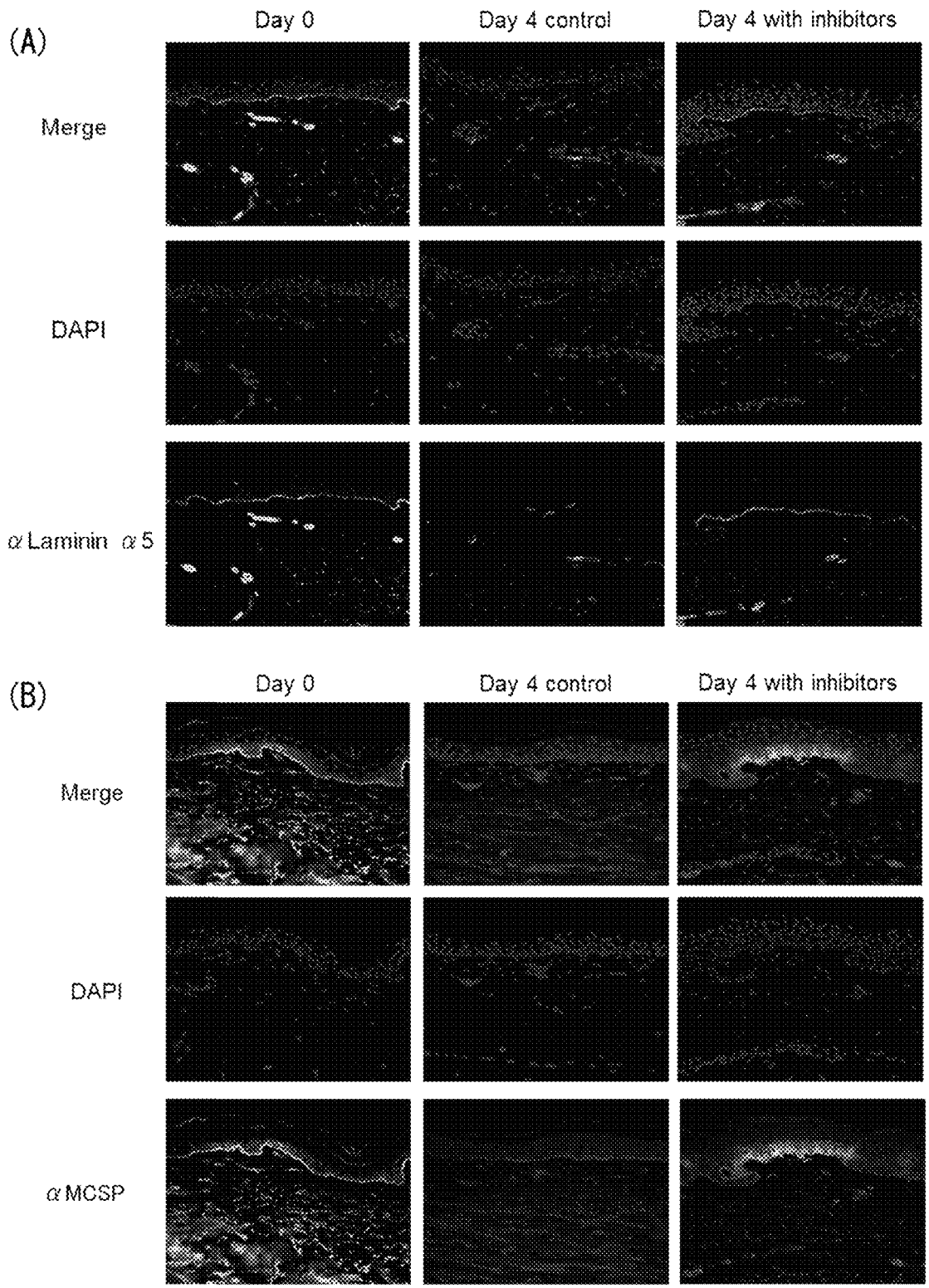
FIG. 4A is a set of photographs showing decrease in laminin 511 by tissue culture of human skin, and augmentation of laminin 511 upon addition of an MMP inhibiting agent (N-hydroxy-2(R)-[[(4-methoxy-phenyl)sulfonyl](3-picolyl)amino]-3-methylbutanamide hydrochloride, hereunder referred to as CGS27023A) and a heparanase inhibiting agent (1-[4-(1H-benzoimidazol-2-yl)phenyl]-3-[4-(1H-benzoimidazol-2-yl)phenyl]urea, hereunder referred to as BIPBIPU).
FIG. 4B is a set of photographs showing reduction in MCSP by tissue culture of human skin, and maintenance or augmentation of MCSP upon addition of an MMP inhibiting agent (CGS27023A) and heparanase inhibiting agent (BIPBIPU).
Figure 6:
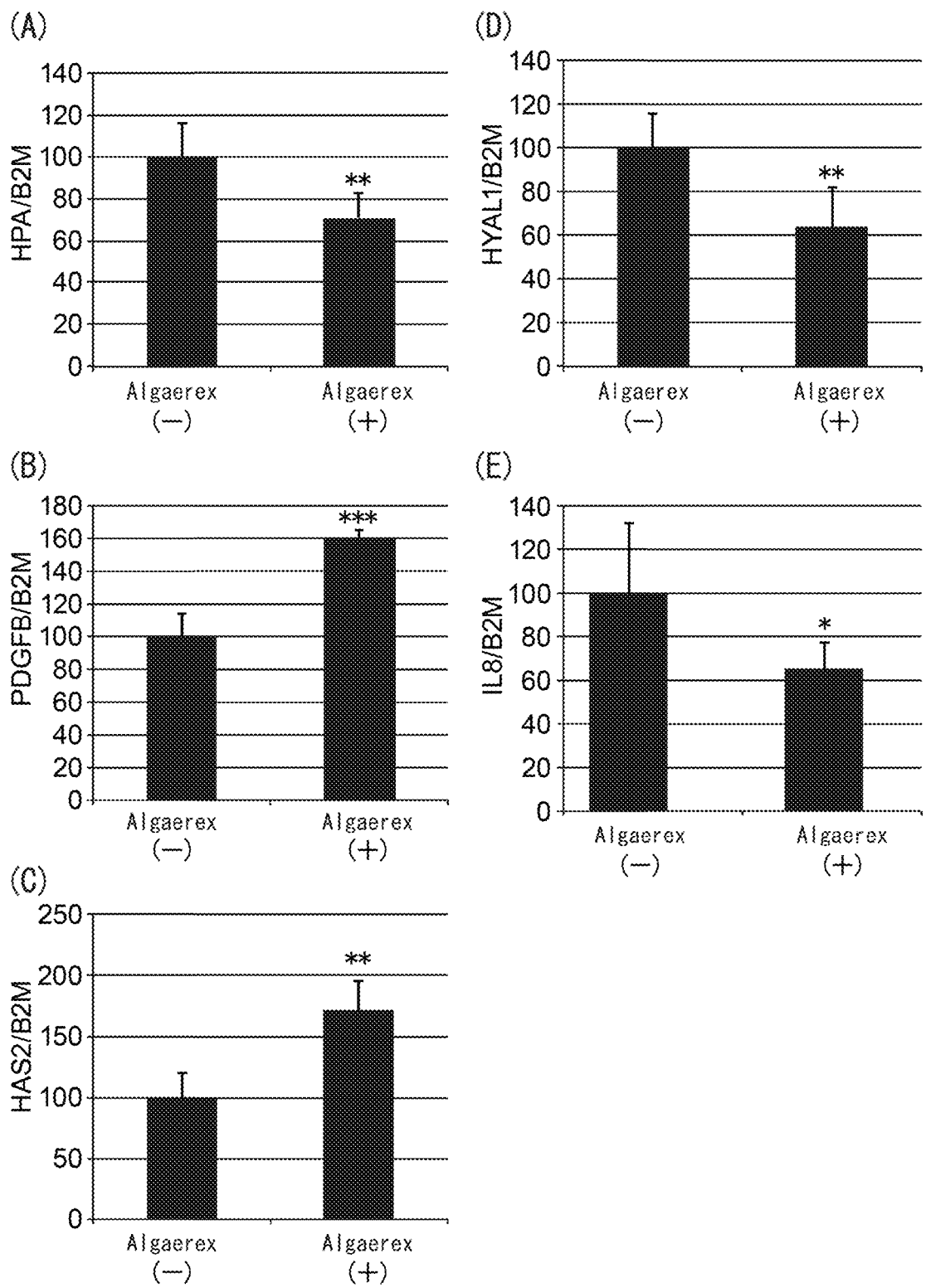
FIG. 6 is a set of graphs showing changes in gene expression by addition of Algaerex. Changes in the expression levels of the heparanase (HPA) gene (FIG. 6A), the PDGF-BB gene (FIG. 6B), the hyaluronic acid synthase 2 (HAS2) gene (FIG. 6C), hyaluronidase 1 (HYAL1) (FIG. 6D) and the interleukin-8 (IL-8) gene (FIG. 6E) were examined.

The present invention relates to a screening method for a laminin 511-expression promoting agent, using the expression level of laminin 511 in epidermal cells as an index. More specifically, the screening method for a laminin 511-expression promoting agent comprises:
a step of culturing epidermal cells in a culture medium containing a candidate drug,
a step of measuring expression of laminin 511 in the epidermal cells, and
a step of judging the candidate drug to have an effect of promoting expression of laminin 511 when expression of laminin 511 has increased compared to an expression level of laminin 511 in a control. The method may further comprise a step of irradiating the cultured epidermis cells with ultraviolet rays. Irradiation with ultraviolet rays causes reduction in laminin 511 expression. As an example of irradiation with ultraviolet rays, the cultured cells may be irradiated with 1 mJ/cm$^2$ to 200 mJ/cm$^2$. Irradiation with ultraviolet rays augments matrix metalloproteinase activity, which results in laminin degradation. Under ultraviolet irradiation, therefore, it can be determined whether a candidate drug has a degradation-inhibiting effect or an expression-promoting effect on laminin 511, when the candidate drug is able to inhibit reduction in the protein level of laminin 511. By examining the inhibiting effect of a candidate drug on matrix metalloproteinase activity, it is possible to determine whether the candidate drug has an effect of promoting expression of laminin 511.

The step of culturing epidermal cells in a culture medium containing a candidate drug may be carried out by any desired system in which the cultured epidermis cells are contacted with the medium containing the candidate drug. The candidate drug or its diluted solution may be added directly to the culturing medium, or the culture medium may be exchanged with one containing the candidate drug. The culturing is carried out under common conditions used for culturing of human epidermis cells. An example is culturing in an incubator in a humidified atmosphere at 37° C., 5% $CO_2$. The culturing time after addition of the candidate drug may be set as desired depending on the effect of the candidate drug. From the viewpoint of adequately exhibiting the effect of the candidate drug, for example, the culturing may be carried out for 300 minutes or longer, preferably 6 hours or longer, and more preferably 48 hours or longer. From the viewpoint of preventing saturation of the effect of the candidate drug, the culturing may be carried out for a period of up to 7 days, preferably no longer than 5 days, and more preferably no longer than 72 hours.

Expression of laminin 511 of cultured epidermis cells may be measured by using antibody that recognizes laminin 511 in accordance with any method employed in molecular biology. The protein level of laminin 511 can be measured using Western blotting or an immunostaining method, for example. Expression of laminin 511 can also be measured based on transcription amounts of mRNA of the constitutional subunits of laminin 511 (α5, β1, γ1). mRNA transcription amounts is measured, for example, by Northern blotting or quantitative PCR. The constitutional subunits can be measured based on the amount of transcription of any one, or the combined transcription amounts of two or three. In one aspect, the expression level of laminin can be measured by summing the expression levels of each of laminin α5, laminin β1 and laminin γ1. In another aspect, the amount of the structural subunit with the lowest expression level may be used as the expression level of laminin 511.

When expression of laminin 511 has increased in comparison to a control expression level of laminin 511, in epidermal cells cultured in culture medium containing a candidate drug, the candidate drug may be judged to have an effect of promoting expression of laminin 511. According to one aspect, the candidate drug may be judged to have an effect of promoting expression of laminin 511 when a significant difference is found in the expression levels. According to another aspect, the candidate drug may be judged to have an effect of promoting expression of laminin 511 when the expression level has increased by a prescribed proportion. The prescribed proportion can be set as desired by a person skilled in the art, but as an example, the prescribed proportion may be set to be 10%, preferably 20%, more preferably 30% and even more preferably 50%, compared to the control expression level. The judgment may be made by the experimenter, or it may be made by software analysis. From the viewpoint of conducting the screening method of the invention on a large scale, the judging step is preferably carried out by the device used to conduct measurement of expression, or by a computer with a processor that has received data from the device. A expression level of laminin 511 in a control is the expression level of laminin 511 in epidermal cells that have been handled in the same manner except for lacking the candidate drug. Thus, the culturing step and expression measuring step may include a step of culturing the control epidermal cells in culture medium lacking the candidate drug, and measuring expression of laminin 511 by the control epidermal cells. The culturing step and expression step for the control may be carried out simultaneously in parallel or before the culturing step and expression step using culture medium containing the candidate drug.

The screening step of the invention may include, in addition to the steps described above, extra optional steps such as a preculturing step carried out before the step of culturing of the epidermal cells in culture medium containing the candidate drug, a post-culturing step in which further culturing is carried out in culture medium lacking the candidate drug, after the step of culturing the epidermal cells in culture medium containing the candidate drug, a recovery step in which the cells are recovered, and a step of storing the recovered cells, or the protein, mRNA or DNA reverse-transcribed from mRNA, that have been extracted from the recovered cells.

Laminin is a protein belonging to the laminin family, which is one of the proteins constituting the basal membrane. Among proteins of the laminin family, laminin 332 composed of the α3β3γ2 subunits and laminin 511 composed of the α5β1γ1 subunits are known to be present in the basal membrane. Laminin is recognized by integrin expressed on cells and functions as a cellular scaffold.

Epidermal basal cells forms layer by using Laminin presented in the basal membrane as a scaffold.

Laminin 511 is a protein involved in cell adhesion and proliferation, and is present mainly in the epidermal basal membrane. Laminin 511 is able to bind to β1 integrins, in particular α6β1 integrin. In cell experiments, it is involved in proliferation of stem cells that express β1 integrin, and is used for culturing of iPS cells and ES cells. In living bodies, laminin 511 is known to decrease with age. The present inventors have demonstrated that decrease in laminin 511 occurs by the influence of ultraviolet rays, in addition to aging (FIG. 1). While it is not intended to be constrained by theory, it is believed that ultraviolet rays activate matrix metalloproteinases (MMP) and thereby cause reduction in laminin. However, the present inventors have also shown that while laminin 332 is less affected by aging and ultraviolet rays, laminin 511 reduced with aging and is also reduced by the effects of ultraviolet rays (FIG. 2A). The same tendency was shown with β1 integrins expressed by stem cells, and a similar tendency was likewise found with MCSP-expressing stem cells (FIG. 1A).

The term "laminin 511-expression promoting agent" is used in the widest possible sense, and it includes any drugs that are able to increase the protein level of laminin 511. Therefore, laminin 511-expression promoting agent are not only drugs that are able to promote gene expression of laminin 511, but also drugs that can increase the protein level of laminin 511 by heparanase-inhibiting and MMP-inhibiting effects. Expression of laminin 511 can be determined based on the protein level or mRNA level. Since laminin 511 is a complex protein, a laminin 511-expression promoting agent is one that can promote expression of each mRNA for the constitutional subunits. A laminin 511-expression promoting agent can increase expression of laminin 511 in the epidermal basal membrane, thus exhibiting epidermal basal membrane stabilizing action, epidermal stem cell reduction inhibiting action, and epidermal stem cell proliferation promoting action. Therefore, a laminin 511-expression promoting agent may be considered to be an epidermal basal membrane stabilizing agent, epidermal stem cell reduction inhibiting agent, or epidermal stem cell proliferation promoting agent.

The epidermal basal membrane is present in the epidermal lowermost layer and constitutes the boundary between the epidermis and the dermis. The epidermal basal membrane is a thin, membranous extracellular matrix composed mainly of collagen, proteoglycan, entactin and laminin. Basal cells are arranged on the basal membrane, and the basal membrane and basal cells are collectively referred to as the basal lamina of the epidermis. The collagen in the basal membrane consists mainly of type I collagen, type IV collagen and type VII collagen. Laminin 511 and laminin 332 are the major laminins in the basal membrane. The basal membrane is partially degraded and destabilized by the effects of extracellular matrix degrading enzymes such as matrix metalloproteinases and heparanase. In the destabilized basal membrane, laminin is reduced, and epidermal cells that proliferate by using laminin as the cell scaffolding, such as β1 integrin-expressing cells, may be lost. Among epidermal cells, the epidermal stem cells and especially epidermal basal stem cells are thought to be β1 integrin-expressing cells, and these cells are lost as laminin is reduced.

Collagen in the dermis differs in shape depending on its location in the dermis, and the types of constituent collagen also differ. The region of the epidermal basal membrane contains type I collagen, type IV collagen and type VII collagen, while thin collagen fiber bundles known as the "lamina fibroreticularis" are located in the region directly under the basal membrane, with finer collagen fibers being located more deeply, and thick collagen fibers being located at the maximum depth. The lamina fibroreticularis in the region directly under the basal membrane is composed mainly of type V collagen, the fine collagen fibers are composed of type III collagen and type V collagen, and the collagen fibers at the maximum depth are composed of type I and type III collagen.

Figure 12B:
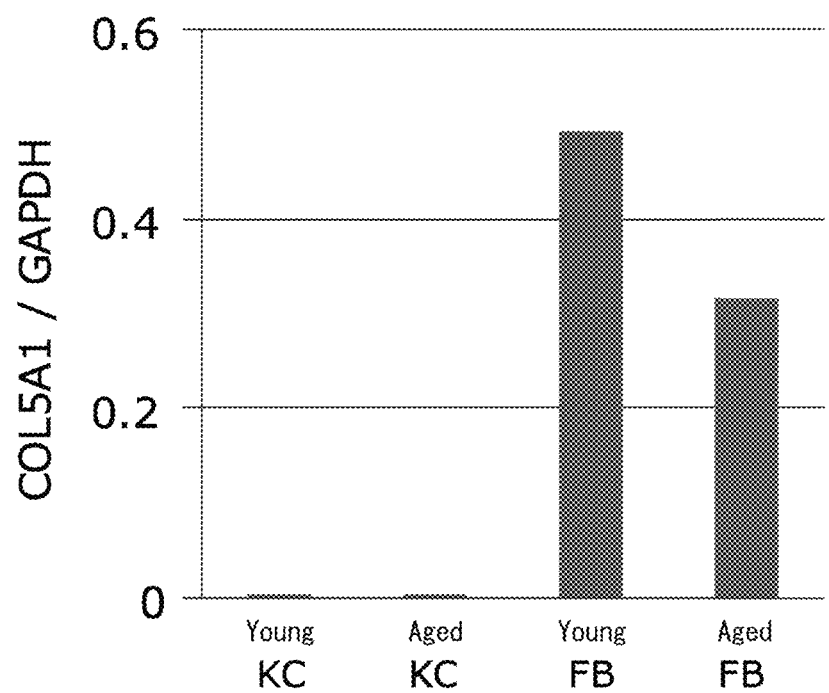
FIG. 12B is a graph showing the expression levels of gene COL5A1 with respect to type V collagen, for keratinocytes and fibroblasts obtained from a young subject, and keratinocytes and fibroblasts obtained from an older subject.
Figure 13A:
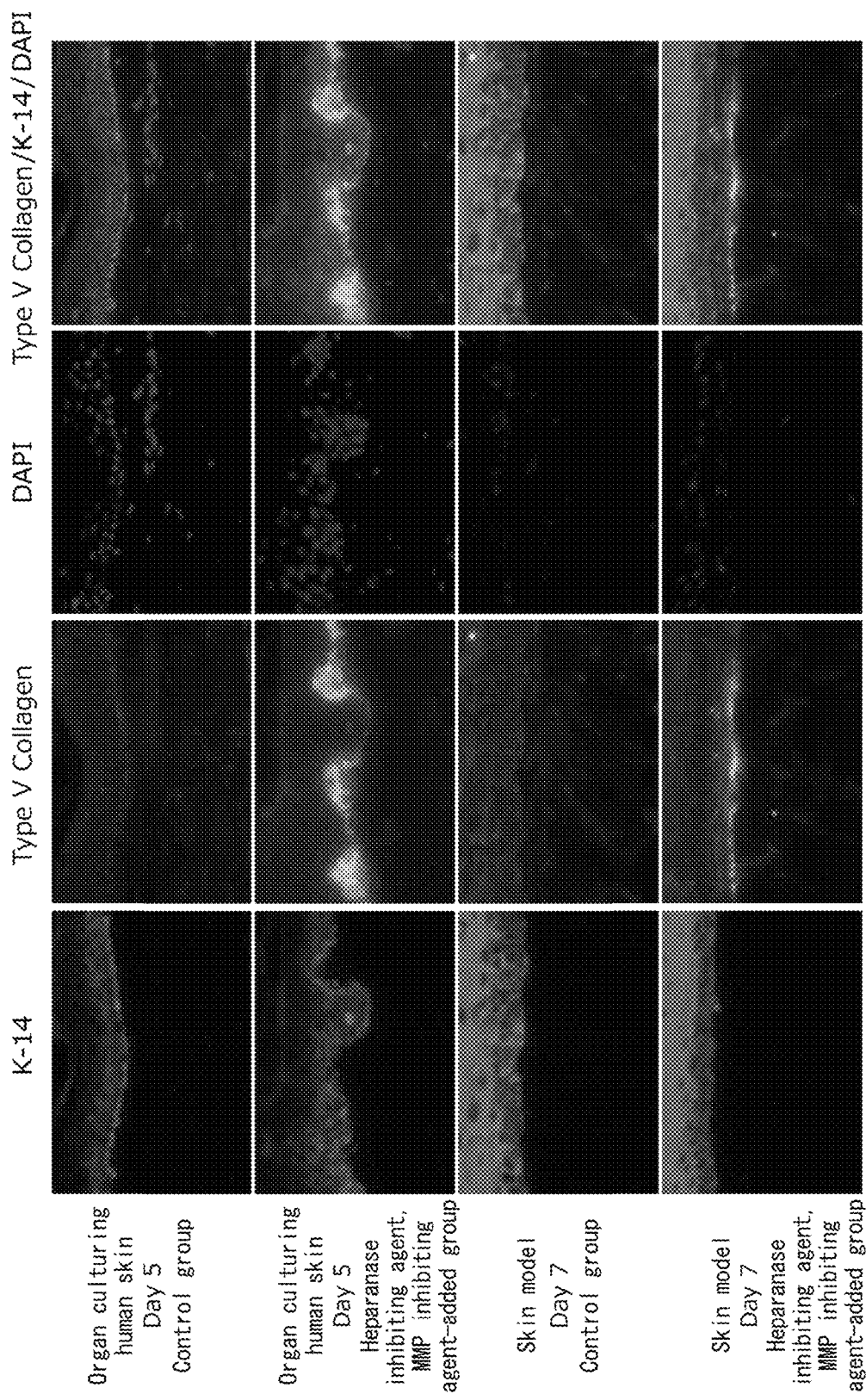
FIG. 13A is a set of fluorescent microscope photographs showing expression of type V collagen and expression of K-14, representing keratinocytes, upon addition of an MMP inhibiting agent (CGS27023A) and a heparanase inhibiting agent (BIPBIPU), in organ culturing of skin tissue and a three-dimensional skin model.
Figure 13B:
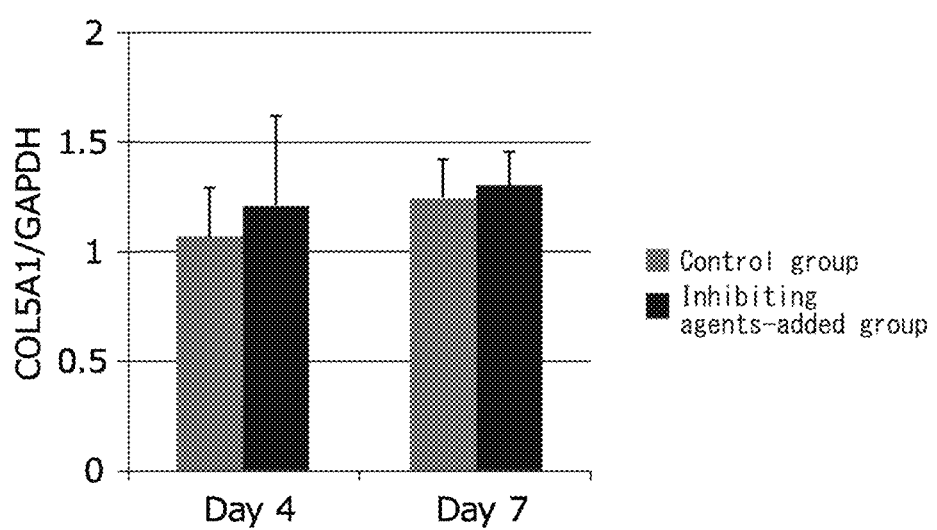
FIG. 13B is a graph showing expression of gene COL5A1 for type V collagen in the dermis of a three-dimensional skin model.
Figure 14:
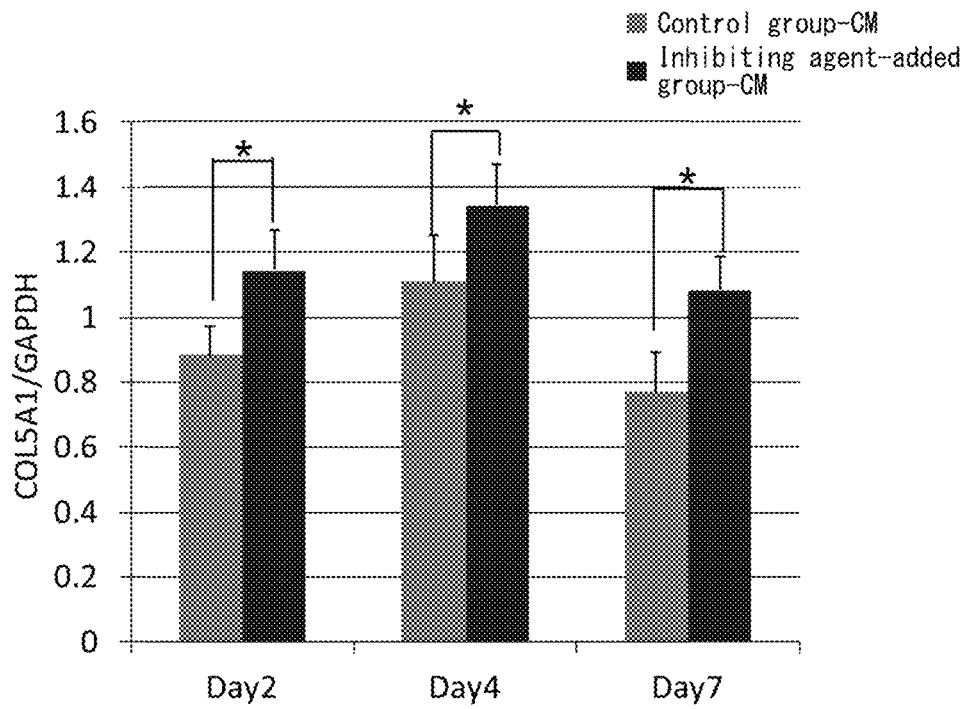
FIG. 14 is a graph showing expression of gene COL5A1 for type V collagen, after addition of a culture supernatant, harvested from a cultured three-dimensional skin model cultured with addition of an MMP inhibiting agent (CGS27023A) and a heparanase inhibiting agent (BI-PBIPU), to cultured dermal fibroblasts.

The type V collagen directly under the basal membrane is produced by dermal fibroblasts in the dermis layer, but research by the present inventors has demonstrated that it decreases in an age-dependent manner (FIG. 12). It has also been found, surprisingly, that the presence of type V collagen is closely related to the presence of the basal membrane (FIG. 13A). On the other hand, the overall amount of collagen production in the dermis layer is not affected by addition of MMP inhibiting agents or heparanase inhibiting agents that protect the basal membrane (FIG. 13B). Based on these results, the present inventors eventually hypothesized that some factor is secreted from the basal membrane side, such that only dermal fibroblasts directly under the basal membrane are activated and produce type V collagen. In order to prove this hypothesis, MMP inhibiting agent and heparanase inhibiting agent that protect the basal membrane were added to a three-dimensional skin model including a dermis layer, basal membrane and epidermal layer, and medium was harvested from the cultured product. The harvested medium was added to cultured fibroblasts culture, and thereby expression of type V collagen was determined (FIG. 14). It was found that the medium obtained from the cultured product containing the added MMP inhibiting agent and heparanase inhibiting agent that protect basal membrane can have an effect of promoting expression of type V collagen.

Figure 15:
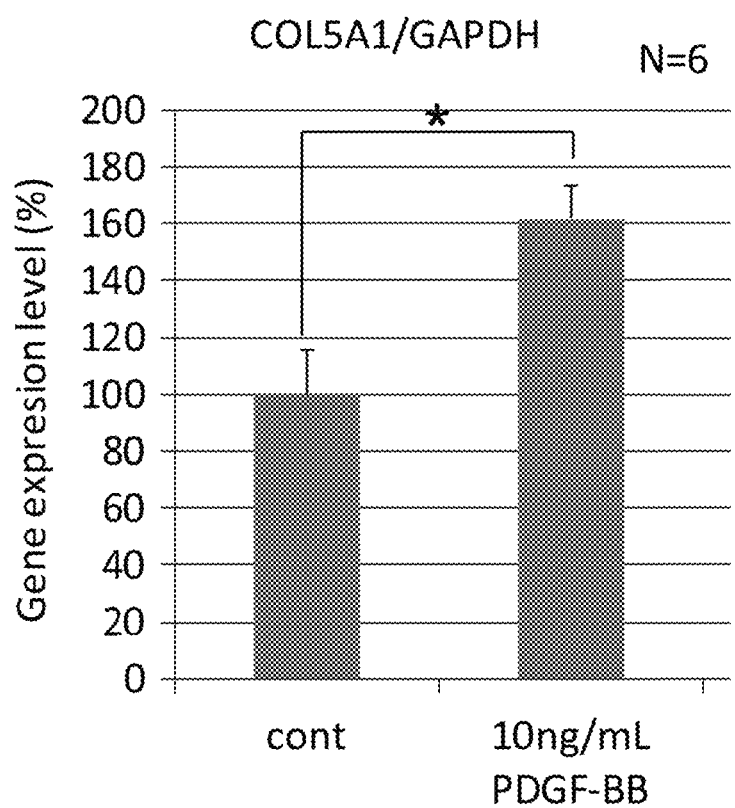
FIG. 15 is a graph showing expression of gene COL5A1 for type V collagen, after addition of PDGF-BB to cultured human fibroblasts.

When the epidermis was harvested from the cultured product of the three-dimensional skin model to which MMP inhibiting agent and heparanase inhibiting agent, which protect the basal membrane, the growth factors which demonstrated altered expression by addition of the inhibiting agents were examined. Then, PDGF-BB was identified as a growth factor having an effect of promoting expression of type V collagen (FIG. 15). PDGFRβ, the receptor for PDGF-BB, was shown to be expressed in dermal fibroblasts directly under the basal membrane. While it is not intended to be constrained by theory, our findings suggest an aging model in which damage to the basal membrane with aging results in lower PDGF-BB production, and consequently lower expression levels of type V collagen, thereby the elasticity of the skin is lost. Referring to this aging model, a laminin 511-expression promoting agent, epidermal basal membrane stabilizing agent, epidermal stem cell reduction inhibiting agent or proliferation promoting agent identified by the present invention may also be considered to be a PDGF-BB production promoting agent, and can be used as a collagen production promoting agent, and most preferably a type V collagen production promoting agent, so that it may be formulated in cosmetics as an elasticity improving agent.

An epidermal basal membrane stabilizing agent is an agent capable of stabilizing the epidermal basal membrane. A basal membrane stabilizing agent may be an inhibiting agent of an extracellular matrix degrading enzyme that degrades the basal membrane, or it may be a promoting agent of expression of a constituent molecule of the basal membrane. Inhibiting agent of extracellular matrix degrading enzymes include heparanase inhibiting agents, known examples of which include drugs such as Mukuroji extract powder, Kanokoso extract E, *Citrus reticulata* extract BG, white lily, longevity grass extract, IBR, S-173 and BIBIPU. Inhibiting agent of extracellular matrix degrading enzymes include matrix metalloproteinase (MMP) inhibiting agent, known examples of which include drugs such as turmeric extract BG, tormentilla extract, mangosteen extract BG and CGS27023A. These can inhibit reduction or cause proliferation of epidermal basal stem cells by stabilizing the epidermal basal membrane. Therefore, an epidermal basal membrane stabilizing agent may also be considered to be an epidermal stem cell reduction inhibiting agent, or proliferation promoting agent. A reduction inhibiting agent or proliferation promoting agent of epidermal basal stem cells is a drug that can exhibit an effect of promoting proliferation of, inhibiting reduction in, or maintaining epidermal basal stem cells. It can also exhibit an anti-aging effect on the epidermis as a reduction inhibiting agent or proliferation promoting agent of epidermal basal stem cells. An epidermal basal membrane stabilizing agent may therefore be considered to be an anti-skin aging agent.

The epidermal stem cell reduction inhibiting agent or proliferation promoting agent of the invention may be considered to be an agent that can inhibit reduction in, maintain, or promote increase in epidermal stem cells in skin. Epidermal stem cells fall in number with age and ultraviolet irradiation, but application of an epidermal stem cell reduction inhibiting agent or proliferation promoting agent of the invention can inhibit reduction in or maintain epidermal stem cells. According to yet another aspect, it can increase the number of epidermal stem cells.

Epidermal cells used for the invention may be cultured epidermis cells. As epidermal cells, a three-dimensional epidermal model obtained by inducing differentiation can be used. The epidermal cells may include keratinocytes, Langerhans cells, Merkel cells, melanocytes and epidermal basal cells, and preferably also include epidermal stem cells. More preferably, the epidermal stem cells are MCSP-expressing epidermal stem cells, i.e. epidermal basal stem cells. In addition to epidermal basal stem cells, epidermal cells are thought to include epidermal stem cells in the bulge region or sebaceous glands, but of these, only epidermal basal stem cells are capable of expressing MCSP. Therefore, MCSP-expressing epidermal stem cells generally refers to epidermal basal stem cells.

The epidermal cells preferably express integrin. The expressed integrin may be α integrin or β integrin. The epidermal stem cells are most preferably cells expressing β1 integrin. The epidermal cells may be cells derived from any animal species, but they are preferably human cells in order to eliminate any effects of different species. Human cultured cells may be taken from an adult, child, suckling, infant, neonate or fetus, but from the viewpoint of using cells containing abundant numbers of basal stem cells, they are preferably taken from a fetus.

Integrin expressed by epidermal cells is a molecule that is present in the cell membrane and functions as an extracellular matrix receptor. Integrin consists of an α chain and a β chain. The α chain has 18 different known types, while the β chain has about 8 different known types. β1 integrin is integrin wherein the β chain is the β1 subunit and the α chain is any subunit. Integrin including the β1 subunit has high binding ability with laminin. Without being limited to theory, it is believed that laminin 511 is lost by effects of aging and ultraviolet rays, resulting in loss of β1 integrin-expressing stem cells, and consequently reduction in the number of MCSP-expressing stem cells.

The candidate drug used may be a drug in any library of cosmetics or pharmaceuticals. Such a library may be any desired library such as a compound library or extract library. Drugs that can increase laminin 511 expression may be selected from among candidate drugs, to screen for laminin 511-expression promoting agents, epidermal basal membrane stabilizing agent, or epidermal basal stem cell reduction inhibiting agents or proliferation promoting agent.

A control is an experimental group having an expression level of laminin 511 serving as a comparison reference, to be used to judge the laminin 511 expression-promoting effect of a candidate drug in a judging step. Thus, the expression level of laminin 511 determined using cells cultured for the same period under the same conditions, but lacking only the candidate drug, is provided for comparison as a control expression level. Such an expression level in a control may be determined by culturing the cells in parallel with the step of culturing the epidermal cells in culture medium containing the candidate drug, and measuring expression of laminin 511, or it may be determined by culturing them separately beforehand under the same conditions for the same time length, and measuring expression of laminin 511.

When the screening method of the invention was carried out for cosmetic materials, Algaerex was selected as a drug having an effect of promoting laminin 511 production. This selected drug is a laminin 511 expression promoting agent, and is also an epidermal basal membrane stabilizing agent, an epidermal basal stem cell reduction inhibiting agent, and an epidermal basal stem cell proliferation promoting agent.

Algaerex is a cosmetic material marketed by Ichimaru Pharcos Co., Ltd., and is a seaweed extract. More specifically, Algaerex is a mixed extract from brown algae, red algae and green algae. It is obtained by mixing brown algae extract, obtained by immersing whole brown algae in 50% 1,3-butylene glycol for 3 days and filtering, with extract of brown algae, red algae and green algae obtained by immersing whole brown algae, red algae and green algae in 50% 1,3-butylene glycol for 3 days and filtering it. Algaerex is thought to improve moisture content and exhibit an inhibiting effect against skin roughening. The brown algae used in Algaerex are *Laminaria* and *Undaria* algae, examples of which are narrow-leaved tangle and wakame. The red algae used in Algaerex are *Grateloupia* algae, examples of which are *Eucheuma serra* and *Grateloupia sparsa*. The green algae used in Algaerex are *Ulva* algae, an example of which is *Ulva linza*.

According to the invention, the seaweed extract is extract obtained from at least one type of algae selected from the group consisting of brown algae, red algae and green algae. According to a more preferred aspect, the seaweed extract is extract from brown algae, red algae and green algae. More preferably, it is extract of brown algae of *Laminaria* and *Undaria*, red algae of *Grateloupia*, and green algae of *Ulva*, and most preferably Algaerex. The solvent used may be any desired solvent, such as water, alcohol, an ether or an ester, either alone or in admixture. An alcohol that is used may be a monohydric alcohol such as methanol, ethanol, propanol or butanol, a dihydric alcohol such as ethylene glycol, propylene glycol or butylene glycol, or a trihydric alcohol such as glycerin. Ethers that may be used include dimethyl ether, diethyl ether, ethyl methyl ether and tetrahydrofuran. Esters that may be used include methyl acetate and ethyl acetate. When used as a mixture, they may be used in any desired mixing ratio. For example, a liquid mixture of water and 1,3-butylene glycol may be in a range of 1:10 to 10:1, and more preferably in a range of 3:10 to 10:3. A 1:1 liquid mixture may also be used. The seaweed extract may be formulated in a cosmetic. For example, an amount of 0.0001% to 10% and preferably 0.001% to 1.0% of seaweed extract may be added to the cosmetic. An example may be addition of 0.01% seaweed extract to a cosmetic such as an essence, cosmetic water, latex or cream, for example.

The seaweed extract of the invention that has been screened as a laminin 511-expression promoting agent exhibits an effect of promoting expression of laminin 511, a stabilizing effect on the basal membrane, and an epidermal stem cell proliferation-promoting and reduction-inhibiting effect. Due to these effects, or independently of them, seaweed extract also suppresses expression of the heparanase gene. It thereby exhibits an ameliorating effect on skin barrier function. Thus, a laminin 511-expression promoting agent containing seaweed extract can also be used as a heparanase gene expression inhibiting agent or skin barrier function ameliorator. In addition, due to these effects or independently of them, a seaweed extract increases expression of the hyaluronic acid synthase 2 gene while also inhibiting expression of the hyaluronidase gene. Skin moisture is thereby improved. A laminin 511-expression promoting agent containing a seaweed extract can therefore also be used as a hyaluronic acid increase promoting agent or skin moisture improving agent. Due to these effects, or independently of them, seaweed extract also increases expression of PDGF-BB. PDGF-BB acts on dermal fibroblasts to promote production of collagen, in particular type V collagen, and therefore a laminin 511-expression promoting agent containing a seaweed extract exhibits an improving effect on elasticity (Seitai Ikogaku, (2017) 55(2): 97-102). PDGF-BB is known to contribute to stabilization of mesenchymal stem cells. Mesenchymal stem cells also include dermal stem cells, and PDGF-BB acts on dermal stem cells to exhibit an ameliorating effect on elasticity. Thus, a laminin 511-expression promoting agent containing seaweed extract can also be used as a PDGF-BB expression promoting agent or elasticity improving agent. Due to these effects, or independently of them, seaweed extract also suppresses expression of IL-8. An inflammation-inhibiting effect is therefore exhibited as a result. Therefore, a laminin 511-expression promoting agent can also be used as an IL-8 expression inhibiting agent and inflammation suppressing agent. A seaweed extract can therefore also be considered to be an improving agent for skin barrier, elasticity, moisture and inflammation, and may be applied to a subject suffering from a problem with or in need of amelioration of skin barrier, elasticity, moisture or inflammation.

According to another aspect, the invention relates to a cosmetic method for improvement in at least one and preferably all of skin barrier, elasticity, moisture and inflammation. The cosmetic method comprises applying a cosmetic containing at least one extract selected from the group consisting of brown algae, red algae and green algae, to a subject suffering from a problem with or in need of amelioration in at least one and preferably all of skin barrier, elasticity, moisture and inflammation. The subject may have at least one, or all, of the following symptoms: 1) reduced hyaluronic acid in the skin, 2) reduced skin barrier function, 3) start of inflammation, 4) reduced amount of fibers in the papillary layer, and 5) reduced PDGF-BB production. According to yet another aspect, a subject suffering from a problem with or in need of improvement in at least one, or all, of skin barrier, elasticity, moisture and inflammation, is also a subject suffering from symptoms such as reduced skin moisture, skin roughening, pigmentation, skin darkening or reduced skin flexibility. In the cosmetic method of the present invention, a suitable amount is applied to the face and body surface of such a subject at least once a day, and preferably at least twice a day. As a particularly preferred mode for the cosmetic method of the invention, it is applied either after bathing, before retiring and/or after waking up. 1-(2-Hydroxyethyl)-2-imidazolidinone (HEI) is a compound represented by the following chemical formula:

[Chemical Formula 1]

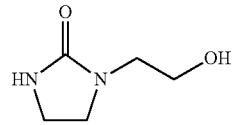

Figure 7:
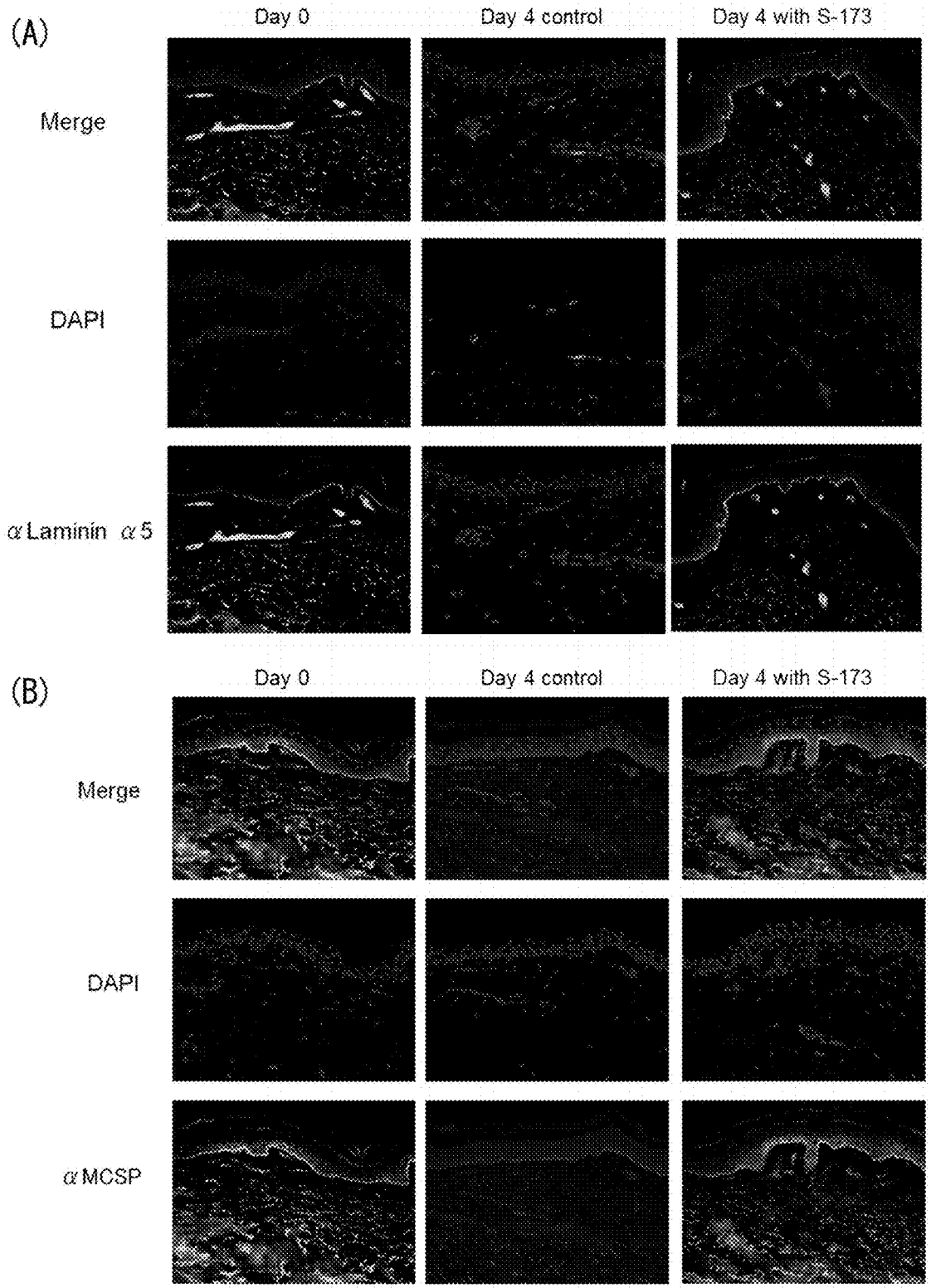
FIG. 7 is a set of photographs showing the effect on laminin 511 and MCSP protein expression by addition of 1-(2-hydroxyethyl)-2-imidazolidinone (HEI) in ex vivo human skin organ culturing.
Figure 8:
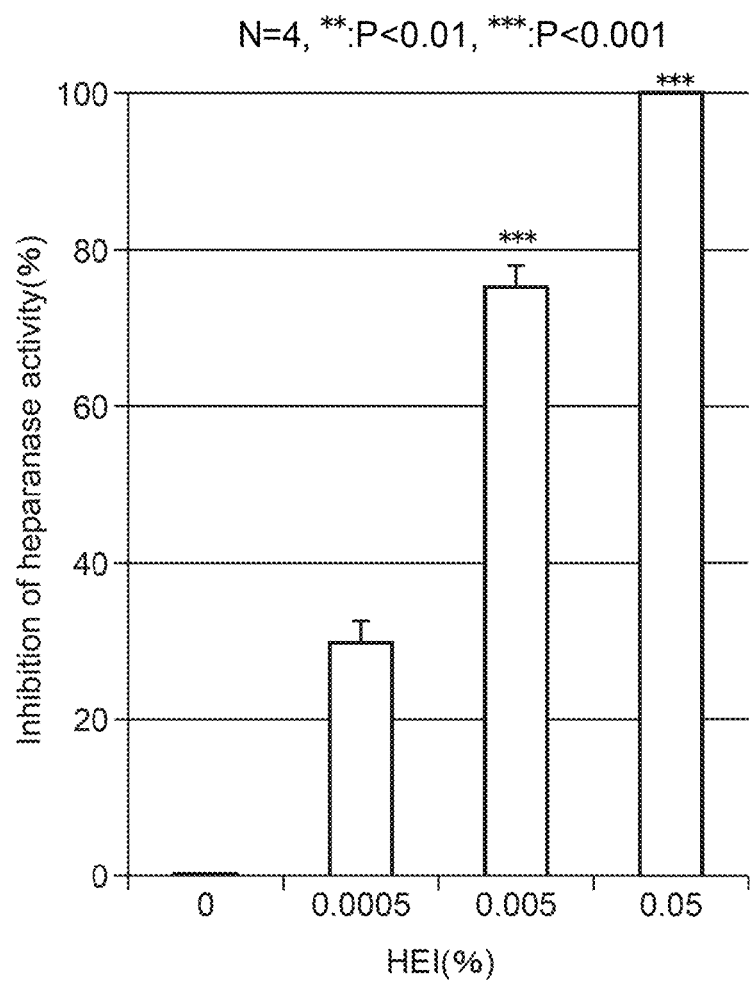
FIG. 8 is a graph showing heparanase inhibition activity of 1-(2-hydroxyethyl)-2-imidazolidinone (HEI).
Figure 9:
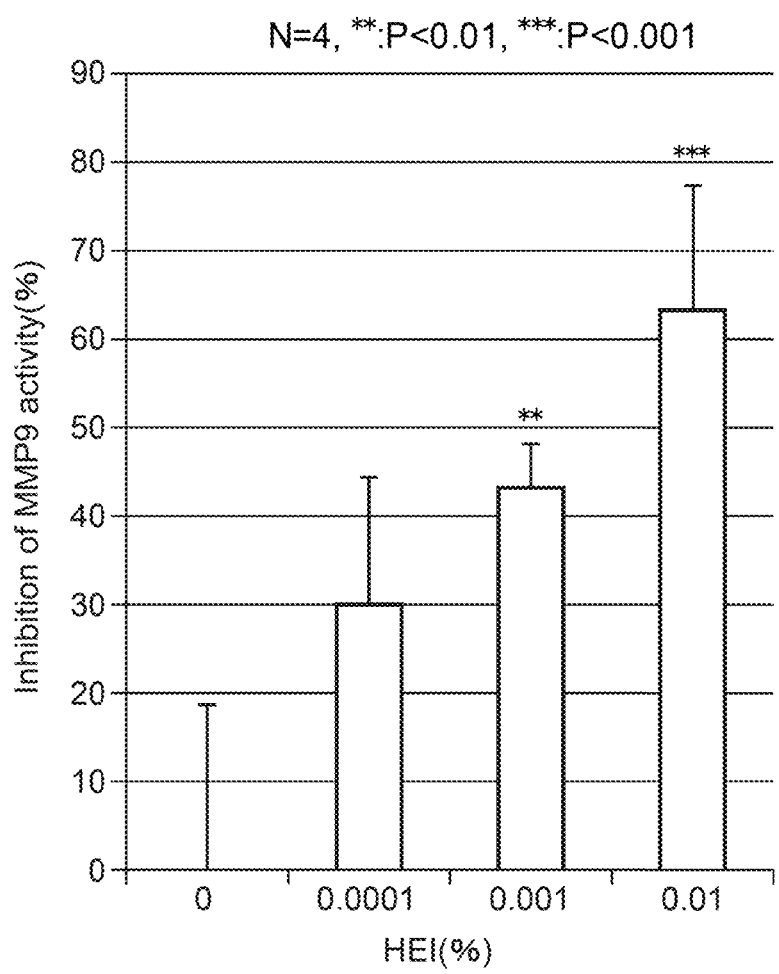
FIG. 9 is a graph showing MMP9 inhibition activity of 1-(2-hydroxyethyl)-2-imidazolidinone (HEI).

HEI has been shown to have heparanase-inhibiting activity and MMP9 inhibiting activity (FIGS. 8 and 9). In addition, HEI has an effect of promoting expression of laminin 511 and an effect of maintaining αMCSP-positive stem cells (FIG. 7). While it is not intended to be constrained by theory, it is possible that heparanase-inhibiting and MMP9-inhibiting activity produces an effect of promoting expression of laminin 511, thereby exhibiting an effect of maintaining αMCSP-positive stem cells. The present invention therefore relates to a laminin 511-expression promoting agent including HEI. Since heparanase and MMP9 are both extracellular matrix degrading enzymes, HEI may also be considered to be an extracellular matrix degrading enzyme inhibiting agent. Heparanase and MMP9 are also known to be utilized when expressed during cancer metastasis. Cancer cells destroy the basal membrane by the action of these enzymes, and enter the blood flow, resulting in metastasis. MMP9 is also involved in angiogenesis. Therefore, an MMP9 inhibiting agent can be used as an angiogenesis inhibiting agent, and thus has a growth inhibiting effect on cancer cells. Therefore, a heparanase and MMP9 activity inhibiting agent and basal membrane stabilizing agent according to the invention may be used not only by being formulated into a cosmetic, but also in a drug as a cancer metastasis inhibiting agent, angiogenesis inhibiting agent or cancer cell growth inhibiting agent. When formulated in a cosmetic or pharmaceutical, it may be added in the range of 0.00001% to 10%, preferably in the range of 0.0001% to 5% and more preferably in the range of 0.001% to 3%, as an example. As one example, it may be added at 1.5% to a cosmetic such as cosmetic water, an essence, a latex or a cream.

A laminin 511 expression promoting agent, epidermal basal membrane stabilizing agent or epidermal basal stem cell reduction inhibiting agent and proliferation promoting agent that have been screened by the present invention may each be added to a cosmetic as cosmetic materials. A cosmetic in which the cosmetic material has been formulated can exhibit an anti-aging effect or anti-ultraviolet ray effect for the epidermis, via promotion of expression of laminin 511 or via stabilization of the epidermal basal membrane, or via inhibition of reduction in or promotion of proliferation in epidermal basal stem cells. It may be formulated into any desired cosmetic, examples of which include essences, cosmetic water, latexes, creams, body milks, bath additives, sunscreens, cosmetic bases, makeup products, lotions, aftershave creams and the like. It may also be formulated into a pharmaceutical or quasi drug. Such a pharmaceutical may be administered by any route such as oral, transdermal, intramuscular or intravenous, but it is preferably administered by transdermal administration from the viewpoint of direct action on the skin. For transdermal administration, it is preferably in the dosage form of an external preparation for skin or a skin patch. It is most preferably formulated into an external preparation for skin. Examples of agents that may generally be added to such cosmetics or pharmaceuticals include humectants, skin whiteners, antioxidants, oil components, ultraviolet absorbers, surfactants, thickeners, alcohols, coloring agents, aromatics, water, solvents, antiseptic agents, preservatives, pH regulators, gelling agents and other active ingredients.

Administration of HEI was confirmed to increase gene expression levels of filaggrin, improve skin barrier function and increase moisture content. These effects are believed to be due to stabilization of the basal membrane by promotion of expression of laminin 511. Reduction in epidermal stem cells may be involved in the epidermal aging phenomenon in a variety of ways. An example of aging of the epidermis is moisture reduction, skin roughening, uneven coloration and reduction in skin elasticity. Such aging phenomena occur due to reduction in hyaluronic acid, reduction in skin barrier function, inflammation and reduction in fiber and PDGF-BB production in the papillary layer, respectively. These aging phenomena can be solved by inhibiting reduction and promoting increase in the number of epidermal basal stem cells. Therefore, a laminin 511-expression promoting agent, an epidermal basal membrane stabilizing agent and an epidermal basal stem cell reduction inhibiting agent or proliferation promoting agent may each be considered to be an anti-aging agent having one or more effects selected from the group consisting of a filaggrin gene expression promoting effect, a skin barrier function-enhancing effect, a moisture content-improving effect, a hyaluronic acid-increasing effect, an inflammation-sedating effect and a papillary layer fiber or PDGF-BB production-promoting effect. In addition, a laminin 511-expression promoting agent, an epidermal basal membrane stabilizing agent and an epidermal basal stem cell reduction inhibiting agent or proliferation promoting agent may each be considered to be a filaggrin gene expression promoting agent, a skin barrier function enhancing agent, a moisture content enhancing agent, a hyaluronic acid-promoting agent, an inflammation sedating agent and a papillary layer fiber or PDGF-BB production promoting agent.

EXAMPLES

Example 1: Measurement of Effects of Changes in Aging and Ultraviolet Rays on MCSP-Positive Epidermal Basal Stem Cells in Human Skin
Samples Skin samples were taken from the face and abdominal regions of subjects between 20 and 70 years of age (9 in their 20s, 10 in their 30s, 10 in their 40s, 9 in their 50s, 10 in their 60s and 9 in their 70s), with informed consent, and were fixed using cold acetone according to the AMeX method, and embedded in paraffin.

The embedded tissue was sliced to a thickness of 3 μm, and stained using melanoma chondroitin sulfate proteoglycan (MCSP) antibody (MAB2029, Chemicon, Billerica, Mass.) as primary antibody and Alexa488-labeled anti-mouse IgG antibody (Life Technologies, Carlsbad, Calif.) as secondary antibody. Nuclear staining was also performed using DAPI, and then staining was performed using anti-α6 integrin antibody (GOH3, Santa Cruz, Dallas, Tex.) as primary antibody and Alexa594-labeled anti-rat IgG antibody (Life Technologies, Carlsbad, Calif.) as secondary antibody. An Olympus BX51 microscope was used for visualization, and an image was taken with a DP-controlled digital camera. FIG. 1A shows the results of staining of the facial regions and abdominal regions of subjects in their 20s and in their 60s.

The results in FIG. 1A show that for the subject in their 20s and the subject in their 60s, the numbers of MCSP-positive basal cells in the basal epidermal layer (hereunder referred to as "epidermal basal stem cells") were reduced due to aging, in both the facial region and the abdominal region. By comparing the facial regions (exposed sections) and the abdominal regions (unexposed sections) of the same subjects, it is seen that the number of epidermal basal stem cells is lower in the facial regions (exposed sections). In addition, the number of epidermal basal stem cells with respect to the length of the basal membrane was also measured for each subject, and the average was represented in a graph (FIG. 1B).

After then culturing keratinocytes taken from subjects in different age groups from 0 to 60, and separating and recovering them, an RNeasy mini kit (QIAGEN, Tokyo, Japan) was used for extraction and purification of the mRNA according to the manufacturer's manual.

The MCSP gene expression level of the keratinocytes was measured by quantitative PCR using a Platinum SYBR Green qPCR Supermix-UDG (Invitrogen Japan, Tokyo Japan). The primers used were the following:

TABLE 1

| Primer name | Sequence |
| --- | --- |
| MCSP-F | CACGGCTCTGACCGACATAG (SEQ ID No. 1) |
| MCSP-R | CCCAGCCCTCTACGACAGT (SEQ ID No. 2) |
| B2M-F | GTGGGATCGAGACATGTAAGCA (SEQ ID No. 3) |
| B2M-R | CAATCCAAATGCGGCATCT (SEQ ID No. 4) |

FIG. 1C shows changes in the expression level for the different age groups.

Based on the results in FIG. 1A it is understood that aging and ultraviolet rays both contribute to reduction in number of epidermal basal stem cells. Furthermore, the results of FIGS. 1B and C demonstrate that aging causes reduction in the number of MCSP-positive cells, as well as a reduction in MCSP expression level.

The embedded tissue was sliced to a thickness of 3 μm, and stained using anti-laminin 332 antibody (prepared, BM165, mouse monoclonal antibody), anti-laminin 511 antibody (4C7, Abacam, Cambridge, UK) and β1 integrin antibody (manufacturer: P5D2, Santa Cruz, Calif.) as primary antibodies and Alexa488-labeled anti-mouse IgG antibody (manufacturer: Life Technologies, Carlsbad, Calif.) as secondary antibody. DAPI was also used for nuclear staining. An Olympus BX51 microscope was used for visualization, and an image was taken with a DP-controlled digital camera. FIG. 2A shows the results of staining of the facial regions and abdominal regions of subjects in their 20s and in their 60s.

After further separating and recovering keratinocytes taken from subjects in different age groups, an RNeasy mini kit (QIAGEN, Tokyo, Japan) was used for extraction and purification of the mRNA according to the manufacturer's manual. The laminin α5 gene expression level of the keratinocytes was measured by quantitative PCR using a Platinum SYBR Green qPCR Supermix-UDG (Invitrogen Japan, Tokyo Japan). The primers used were the following:

TABLE 2

| Primer name | Sequence |
|---|---|
| LAMA5-F | TGGCTGGATTATGTACTCGTGG (SEQ ID No. 5) |
| LAMA5-R | CTGTAGCACCTACTTCGTGGCA (SEQ ID No. 6) |
| B2M-F | GTGGGATCGAGACATGTAAGCA (SEQ ID No. 3) |
| B2M-R | CAATCCAAATGCGGCATCT (SEQ ID No. 4) |

FIG. 2B shows changes in the expression level for the different age groups. Based on the results of FIGS. 1A to C and FIGS. 2A and 2B, it is seen that the same tendency was exhibited for expression levels of laminin 551 and β1 integrin and number of epidermal basal stem cells, in terms of the effects of aging and ultraviolet rays.

Example 2: Connection Between Laminin 511 and Stem Cell Markers

Human epidermis keratinocytes were cultured for 6 days using Humedia-KG2 culture medium (Kurabo Co., Ltd, Japan), in a Primeria flask (Coaster, Tokyo, Japan) coated with iMatrix-511 (Wako Pure Chemical Industries, Ltd.). Culturing was also carried out in a non-coated flask as a control. Cells grown to subconfluence were removed with trypsin (Nakarai Co., Ltd., Japan), seeded on an iMatrix-511-coated chamber slide (Thermo Fisher Science, Waltham, Mass.), and cultured. The control group was cultured on a non-coated chamber slide.

After culturing, the cells were fixed with 4% PFA, and stained using MCSP antibody (MAB2029, Chemicon, Billerica, Mass.) as primary antibody and Alexa488-labeled anti-mouse IgG antibody (Life Technologies, Carlsbad, Calif.) as secondary antibody. DAPI was also used for nuclear staining. An Olympus BX51 microscope was used for visualization, and an image was taken with a DP-controlled digital camera. In the iMatrix511-coated group, the MCSP-positive cells were more abundantly maintained compared to the non-coated control (FIG. 3A).

The medium after culturing was discarded, and rinsing was performed with PBS. An RNeasy mini kit (QIAGEN, Tokyo, Japan) was used for extraction and purification of the mRNA from the cells according to the manufacturer's manual. Quantitative PCR was conducted using Platinum SYBR Green qPCR Supermix-UDG (Invitrogen Japan, Tokyo Japan), for measurement of the expression levels of genes for the stem cell markers CD46, DLL1, Lrig1 and CD44. The primers used were the following:

TABLE 3

| Primer name | Sequence |
|---|---|
| CD46-F | CTTTGTAGTCTCTGGCAAGATGC (SEQ ID No. 7) |
| CD46-R | CGGGTATAAACTTCAACTCTGTGC (SEQ ID No. 8) |

TABLE 3-continued

| Primer name | Sequence |
|---|---|
| DLL1-F | TCCAAGGATATATGCCCCAA (SEQ ID No. 9) |
| DLL1-R | GAACTCGGTTTCTCAGCAGC (SEQ ID No. 10) |
| Lrig1-F | CTTGACCTGGGTTCTGGGTA (SEQ ID No. 11) |
| Lrig1-R | GGCCAAAGGAACATTTGAAG (SEQ ID No. 12) |
| CD44-F | TTGCAGTCAACAGTCGAA (SEQ ID No. 13) |
| CD44-R | TTCTGACGACTCCTTGTTC (SEQ ID No. 14) |
| B2M-F | GTGGGATCGAGACATGTAAGCA (SEQ ID No. 3) |
| B2M-R | CAATCCAAATGCGGCATCT (SEQ ID No. 4) |

In the laminin 511-coated group, expression levels of the genes for CD46, DLL1, Lrig1 and CD44 were increased (FIG. 3B) compared to expression levels of the genes for CD46, DLL1, Lrig1 and CD44 in the control, indicating that laminin 511 contributes to maintenance of stem cells.

Example 3: Maintaining Numbers of MCSP-Positive Epidermal Basal Stem Cells by Addition of Laminin Degradation Inhibiting Agent Skin samples were taken from the abdominal regions of subjects (20 to 30 years of age), with informed consent. The taken samples were cultured for 4 days in culture medium containing the MMP9 inhibiting agent CGS270234 (10 μM) and the heparanase inhibiting agent BIPBIU (10 μM). The culture medium was William's E medium (Thermo Fisher Science, Waltham, Mass.). CGS270234 and BIPBIU are compounds represented by the following respective chemical formulas, and their use as MMP9 inhibiting agents and heparanase inhibiting agents is known (Iriyama S, et al., Exp Dermatol. 2011; 20 (11): 953-5).

[Chemical Formula 2]

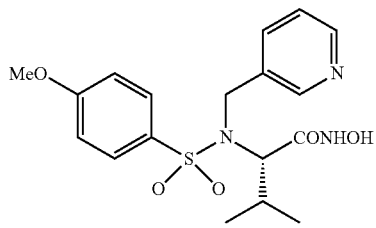

(CGS27023A; a MMP inhibitor)
N-hydroxy-2(R)-[[(4-methoxyphenyl)sulfonyl](3-picolyl)-amino]-3-methylbutanamide hydrochloride

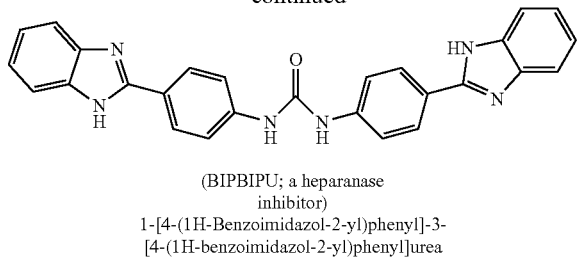

(BIPBIPU; a heparanase inhibitor)
1-[4-(1H-Benzoimidazol-2-yl)phenyl]-3-[4-(1H-benzoimidazol-2-yl)phenyl]urea Skin samples before culturing, samples after 4 days of culturing (control: DMSO solvent added in an equal amount), and samples after 4 days of culturing (drug-added) were fixed using cold acetone according to the AMeX method, and embedded in paraffin.

The embedded tissues were sliced to 3 μm, and co-stained using anti-laminin 551 antibody (4C7, Abacam, Cambridge, UK) as primary antibody and then using Alexa488-labeled anti-mouse IgG antibody (manufacturer: Life Technologies, Carlsbad, Calif.) as secondary antibody. DAPI was also used for nuclear staining. The results are shown in FIG. 4(A). The embedded skin samples were then co-stained using anti-MCSP antibody (MAB2029, Chemicon, Billerica, Mass.) as primary antibody, and then using Alexa488-labeled anti-mouse IgG antibody (Life Technologies, Carlsbad, Calif.) as secondary antibody. DAPI was also used for nuclear staining. The results are shown in FIG. 4(B).

It was shown that 4 days of tissue culturing resulted in decreased laminin 551 in the basal membrane, and also reduced MCSP-positive cells, compared to the non-cultured group (Day 0) and the non-drug-added group (Day 4: Control) as the control. However, when culturing was carried out with addition of an inhibiting agent of matrix metalloproteinase 9 (MMP9) and heparanase inhibiting agent, which degrade laminin, laminin 551 was maintained and MCSP-positive cells were also maintained.

Example 4: Screening of Drugs with Laminin 511 Production-Promoting Effects

Epidermal cells taken from a fetus were cultured for 6 days using Humedia-KG2 culture medium (Kurabo Co., Ltd., Japan), in a Primeria flask (Coaster, Tokyo, Japan) coated with iMatrix-511 (Wako Pure Chemical Industries, Ltd.). When the cells reached subconfluence, the cells were removed with trypsin and seeded on a 6-well plate, and after 1 day, the medium was exchanged with medium dissolving a candidate drug, and culturing was continued for 48 hours. The candidate drugs used were 178 registered cosmetic ingredient materials (of which 135 were extracts and 43 were simple compounds). The medium was discarded, rinsing was performed with PBS, and an RNeasy mini kit (QIAGEN, Tokyo, Japan) was used for extraction and purification of the mRNA according to the manufacturer's manual. The laminin α5, laminin β1 and laminin γ1 gene expression levels were measured by quantitative PCR using a Platinum SYBR Green qPCR Supermix-UDG (Invitrogen Japan, Tokyo Japan). The primers used were the following:

TABLE 4

| Primer name | Sequence |
|---|---|
| LAMA5-F | TGGCTGGATTATGTACTCGTGG (SEQ ID No. 5) |
| LAMA5-R | CTGTAGCACCTACTTCGTGGCA (SEQ ID No. 6) |
| LAMB1-F | TTGGACCAAGATGTCCTGAG (SEQ ID No. 15) |
| LAMB1-R | CAATATATTCTGCCTCCCCG (SEQ ID No. 16) |
| LAMC1-F | GTGCTGTTGTTCCCAAGACA (SEQ ID No. 17) |
| LAMC1-R | GCCATCATCACAGAGCTCAC (SEQ ID No. 18) |
| B2M-F | GTGGGATCGAGACATGTAAGCA (SEQ ID No. 3) |
| B2M-R | CAATCCAAATGCGGCATCT (SEQ ID No. 4) |

Algaerex (Ichimaru Pharcos Co., Ltd.) was found to be a candidate drug that increased expression levels of all of the laminin α5, laminin β1 and laminin γ1 genes compared to the laminin α5, laminin β1 and laminin γ1 gene expression levels of the control.

The screened Algaerex was tested at different drug concentrations of 0.001%, 0.01% and 0.10%, to determine the dose-dependent effect of promoting expression of laminin 511. The cells, culture medium, culturing conditions and PCR conditions employed were the same as in the drug screening method of Example 4. The results are shown in FIG. 5A. Anti-laminin 511 antibody (manufacturer: Cloud-Clone Corp) was also used under the same conditions for protein quantitation analysis by ELISA. The results are shown in FIG. 5B.

Example 5: Verification of Skin Improving Function of Algaerex

Epidermal cells taken from a fetus were cultured using Humedia-KG2 culture medium (Kurabo Co., Ltd., Japan), in a Primeria flask (Coaster, Tokyo, Japan) coated with iMatrix-511 (Wako Pure Chemical Industries, Ltd.). When the cells reached subconfluence, the cells were removed with trypsin and seeded onto a 6-well plate, and after 1 day, the medium was exchanged with medium containing 0.01% Algaerex, and culturing was continued for 48 hours. Algaerex-free medium was used as a control. The medium was discarded, rinsing was performed with PBS, and an RNeasy mini kit (QIAGEN, Tokyo, Japan) was used for extraction and purification of the mRNA according to the manufacturer's manual. Expression levels of the heparanase (HPA) gene, PDGF-BB gene, hyaluronic acid synthase 2 (HAS2) gene, hyaluronidase 1 (HYAL1) and interleukin-8 (IL-8) gene were determined by quantitative PCR using Platinum SYBR Green qPCR Supermix-UDG (Invitrogen Japan, Tokyo Japan). The primers used were the following:

TABLE 5

| Primer name | Sequence |
|---|---|
| HPA-F | CGCGTAGTGATGCCATGTAACTGAA (SEQ ID No. 19) |
| HPA-R | CGCTTCGATCCCAAGAAGGAATCAA (SEQ ID No. 20) |

TABLE 5-continued

| Primer name | Sequence |
|---|---|
| PDGFB-F | CCTGGCATGCAAGTGTGA (SEQ ID No. 21) |
| PDGFB-R | CGAATGGTCACCCGAGTTT (SEQ ID No. 22) |
| HAS2-F | TCAGAGCACTGGGACGAAG (SEQ ID No. 23) |
| HAS2-R | CCCAACACCTCCAACCAT (SEQ ID No. 24) |
| HYAL1-F | GCACAGGGAAGTCACAGATGTATGTC (SEQ ID No. 25) |
| HYAL2-R | CCACTGGTCACGTTCAGGATGAAG (SEQ ID No. 26) |
| IL-8-F | GGGTACCCAGTTAAATTTTCATTTC (SEQ ID No. 27) |
| IL-8-R | CAAGTTTCAACCAGCAAGAAATTACT (SEQ ID No. 28) |

The changes in expression levels are shown in FIGS. 6A to E. In cultured epidermis cells, Algaerex significantly reduced heparanase (HPA) gene expression (p<0.01), significantly increased PDGF-BB gene expression (p<0.001), significantly increased hyaluronic acid synthase 2 (HAS2) gene expression (p<0.01), significantly reduced hyaluronidase 1 (HYAL1) gene expression (p<0.01) and reduced interleukin-8 (IL-8) gene expression (p<0.05).

Example 6: Effect of HEI for Inhibiting Laminin Degradation and Maintaining MCSP-Positive Epidermal Basal Stem Cells Skin samples were taken from the abdominal regions of subjects (20 to 30 years of age), with informed consent. The taken samples were cultured for 5 days in culture medium containing 0.01% 1-(2-hydroxyethyl)-2-imidazolidinone (HEI, or S-173). The culture medium was William's E medium (Thermo Fisher Science, Waltham, Mass.). The control was cultured using HEI-free culture medium. The cultured skin samples were fixed using cold acetone according to the AMeX method, and embedded in paraffin.

The embedded tissue was sliced to 3 μm, and stained using MCSP antibody (MAB2029, Chemicon, Billerica, Mass.) as primary antibody and Alexa488-labeled anti-mouse IgG antibody (Life Technologies, Carlsbad, Calif.) as secondary antibody. Nuclear staining was also performed using DAPI, and then staining was performed using anti-laminin 551 antibody (4C7, Abacam, Cambridge, UK) as primary antibody and Alexa488-labeled anti-mouse IgG antibody (Life Technologies, Carlsbad, Calif.) as secondary antibody. An Olympus BX51 microscope was used for visualization, and an image was taken with a DP-controlled digital camera, and is shown in FIG. 7A. With the control, culturing resulted in reduced laminin 511 and also a reduced MCSP-positive cell count. On the other hand, when culturing with addition of 0.01% HEI, the amount of laminin 511 was maintained and the MCSP-positive cell count on the basal membrane was also maintained.

Example 7: Heparanase Inhibiting Effect of HEI

A heparanase assay was carried out using a heparan sulfate immobilization plate, as described in Behzad F, et al., Analytical Biochemistry, 320, pp. 207-213, 2003. Specifically, heparan sulfate (Seikagaku, Tokyo, Japan) was reacted with photobiotin to prepare biotinylated heparan sulfate. The biotinylated heparan sulfate was fixed onto a carbohydrate-binding surface plate (Coastar, Tokyo, Japan). A431 cell lysate (50 μg/ml) and 0% HEI, 0.0005% HEI, 0.005% HEI or 0.05% HEI were added onto the biotinylated heparan sulfate immobilized plate, incubated for 3 hours at 37° C., and then rinsed with PBS-T. Next, peroxidase-avidin (Vector Laboratories, Inc. CA, USA) was incubated at 37° C. for 1 hour. A 3,3',5,5'-tetramethylbenzidine (TMB) solution (Bio-Rad, Tokyo, Japan) was added, and the plate was further incubated at room temperature for 30 minutes. The absorbance at 450 nm was measured to determine the heparanase inhibiting effect. HEI was shown to inhibit heparanase activity in a dose-dependent manner (FIG. 8).

Example 8: MMP9-Inhibiting Effect of HEI

An MMP9 assay was carried out using a Matrix Metalloproteinase-9 (MMP-9) colorimetric drug discovery kit (Enzo Life Sciences Inc.). Specifically, HEI was added to a recombinant human MMP-9 enzyme solution to 0.0001%, 0.001% and 0.01% concentration. After mixing with chromogenic MMP-9 substrate, the absorbance at 412 nm was measured every other minute. The MMP-9 inhibition rate (%) for HEI was calculated from the slope of the absorbance (OD/min). HEI was shown to inhibit MMP9 activity in a dose-dependent manner (FIG. 9).

Example 9: Epidermis-Improving Effect of HEI

Skin samples were taken from the abdominal regions of subjects (20 to 30 years of age), with informed consent. The taken samples were cultured for 5 days in culture medium containing 0.01% HEI. The culture medium was William's E medium (Thermo Fisher Science, Waltham, Mass.). The control was cultured using HEI-free culture medium. The excess moisture adhering to the cultured skin sample was wiped off with a Kimtowel, and after allowing it to stand for 5 minutes, a Vapometer was used for TEWL measurement, and a Corneometer was used to measure the stratum corneum moisture content. The results are shown in FIGS. 10B and C. The cultured skin samples were fixed using cold acetone according to the AMeX method, and embedded in paraffin.

The embedded tissue was sliced to 3 μm and stained using filaggrin antibody (manufacturer: AKH-1, Santa Cruz Biotechnology, Dallas, Tex.) as primary antibody and Alexa488-labeled anti-mouse IgG antibody (Life Technologies, Carlsbad, Calif.) as secondary antibody. DAPI was also used for nuclear staining. An Olympus BX51 microscope was used for visualization, and an image was taken with a DP-controlled digital camera, and is shown in FIG. 10A.

Next, 20 males from 20 to 50 years of age were asked to apply a 1.5% HEI solution on one side of the face and water on the other side of the face, twice a day for 4 weeks. Before application, 2 weeks after application and 4 weeks after application, the TEWL was measured using a Vapometer, and a Corneometer was used to measure the stratum corneum moisture content. The results are shown in FIGS. 10D and E.

In the HEI-added group, a tendency for increase in filaggrin was seen in ex vivo experimentation. The TEWL decreased in both the ex vivo and in vivo experimentation, and therefore the skin barrier function was improved and the stratum corneum moisture content also increased.

Example 10: Change in Collagen Directly Under Basal Membrane by Addition of MMP Inhibiting Agent and Heparanase Inhibiting Agent Skin tissue slices were prepared from skin tissue purchased from Bio Predic Co. and cultured in William's E medium containing added CGS27023A (final concentration:

$10^{-5}$ M) and BIPBIPU (final concentration: $10^{-5}$ M). As a control, culturing was also carried out without adding the inhibiting agents. The medium was exchanged daily, and skin tissue slices were collected on the 5th day of culturing. The collected skin tissue slices were immersed in Zamboni fixing solution and post-fixed with 1% osmium. The skin samples were embedded in an epoxy resin. Ultrathin sections were prepared and observed under a transmission electron microscope (JEOL JEM1230) (FIG. 11A).

Six skin slices were observed for each group, and 30 photographs were taken of each slice. The sizes and numbers of the collagen fibers in the dermis portions of all of the photographs were calculated using "Win ROOF 2013" image analysis software, and a histogram was prepared (FIG. 11B). The "Win ROOF 2013" image analysis software was likewise used to extract the area of the dermis, and the density of the collagen fibers and the thickness per fiber in the dermis were calculated and the mean values were determined (FIG. 11C).

Example 11: Expression of Type V Collagen

Skin purchased from Bio Predic Co. was supplied to the AMeX method to prepare a paraffin block. Slices of 3 µm thickness were prepared and subjected to fluorescent immunostaining using antibody for type V collagen (Origene Co., Cat #: AM1015PU-N) and antibody for cytokeratin 14 (K-14) (Fitzgerald, Cat #: 20R-CP002) (FIG. 12A). The basal membrane region was stained by cytokeratin 14, with type V collagen appearing directly under it, and the amount decreased with aging.

Normal human epidermis cells and normal human fibroblasts were purchased from Kurabo and Bio Predic Co. Six specimens taken from subjects from 20 to 30 years of age and six specimens taken from subjects 50 to 60 years of age were purchased. The epidermal cells were cultured in serum-free Humedia-KG2 medium, and the fibroblasts were cultured in DMEM medium containing 10% serum. After one subculturing, each sample was seeded in a 6-well plate. Upon reaching confluence, each of the cells were collected and cDNA was prepared, and the following primers were used for real-time PCR to evaluate the gene expression levels of the gene COL5A1 for type V collagen (FIG. 12B). Type V collagen was not expressed by the epidermal cells but was expressed by the fibroblasts, the expression levels being reduced with aging.

TABLE 6

| Primer | Sequence |
|---|---|
| Type V Collagen F | GTGGCACAGAATTGCTCTCA (SEQ ID No. 29) |
| Type V Collagen R | TCACCCTCAAACACCTCCTC (SEQ ID No. 30) |
| GAPDH F | GAAGGTGAAGGTCGGAGTC (SEQ ID No. 31) |
| GAPDH R | GAAGATGGTGATGGGATTTC (SEQ ID No. 32) |

Skin tissue slices were prepared from skin tissue purchased from Bio Predic Co. and cultured in William's E medium containing added CGS27023A (final concentration: $10^{-5}$ M) and BIPBIPU (final concentration: $10^{-5}$ M). As a control, culturing was also carried out without adding the inhibiting agents. The medium was exchanged daily, and skin tissue slices were collected on the 5th day of culturing. The collected skin tissue slices were supplied to the AMeX method to prepare a paraffin block. Slices of 3 µm thickness were prepared and subjected to fluorescent immunostaining using antibody for type V collagen (Origene Co., Cat #: AM1015PU-N) and antibody for cytokeratin 14 (K-14) (Fitzgerald, Cat #: 20R-CP002) (FIG. 13A).

A three-dimensional skin model (EFT-400) purchased from MatTeK was cultured in special medium (EFT400-ASY) containing added CGS27023A (final concentration: $10^{-5}$ M) and BIPBIPU (final concentration: $10^{-5}$ M). As a control, culturing was also carried out without adding the inhibiting agents. The medium was exchanged once every 2 days, and a tissue slice was collected on the 7th day and supplied to the AMeX method, to prepare a paraffin block. Slices of 3 µm thickness were prepared and subjected to fluorescent immunostaining using antibody for type V collagen (Origene Co., Cat #: AM1015PU-N) and antibody for cytokeratin 14 (K-14) (Fitzgerald, Cat #: 20R-CP002) (FIG. 13A).

Groups with an inhibiting agent added and not-added (control) to the three-dimensional skin model were cultured for 4 days and 7 days each. After culturing, the epidermis was removed, the dermis alone was placed in Trizol, and the mRNA was extracted. The cDNA was rapidly prepared, and the aforementioned primers were used for real-time PCR to evaluate the gene expression levels of the gene COL5A1 for type V collagen (FIG. 13B).

In both the skin tissue organ culturing and three-dimensional skin model, type V collagen expression increased with addition of the MMP inhibiting agent and heparanase inhibiting agent, compared to the control. In the total dermis layer, however, no significant change in type V collagen expression was seen by addition of the MMP inhibiting agent and heparanase inhibiting agent.

Figure 13C:
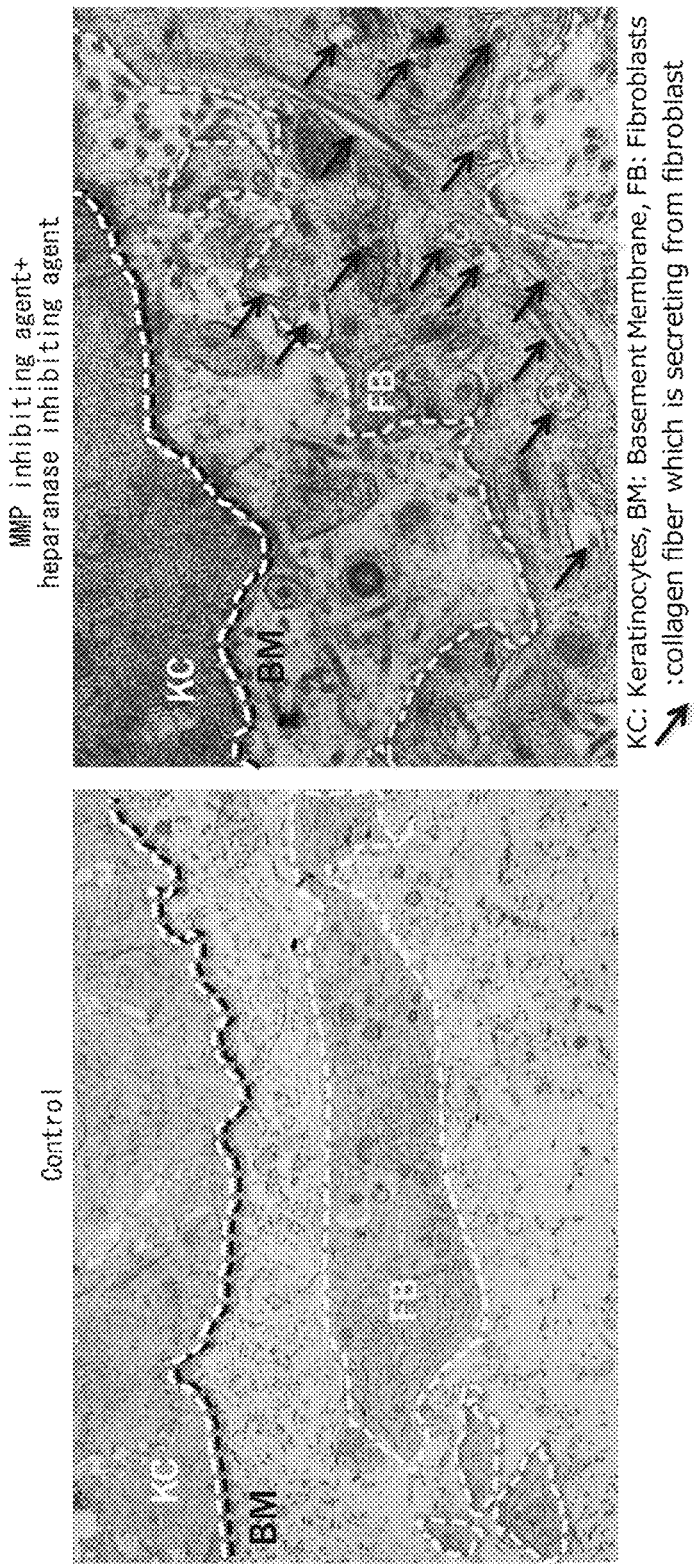
FIG. 13C is a pair of electron micrographs focused on fibroblasts directly under the basal membrane, taken after addition of an MMP inhibiting agent (CGS27023A) and a heparanase inhibiting agent (BIPBIPU) in organ culturing of skin tissue.

In the TEM images of Example 10, focus is on the fibroblasts present directly under the basal membrane (FIG. 13C). In the control shown in FIG. 13C (inhibiting agent-free group), almost no collagen fibers are seen in the fibroblasts, whereas in the inhibiting agent-added group, collagen fibers are seen in the vesicles inside the fibroblasts. The vesicles are suggestive of a process of collagen secretion. This suggests that fibroblasts directly under the basal membrane actively produce collagen by addition of an MMP inhibiting agent and heparanase inhibiting agent.

A three-dimensional skin model (EFT-400) purchased from MatTeK was cultured in special medium (EFT400-ASY) containing added CGS27023A (final concentration: $10^{-5}$ M) and BIPBIPU (final concentration: $10^{-5}$ M). As a control, culturing was also carried out without adding the inhibiting agents. On the 2nd day, 4th day and 7th day of culturing, the culture supernatant was sampled. Separately, normal human fibroblasts from skin harvested from 14-month-old children that had been purchased from Bio Predic Co. were cultured for 24 hours in 10% FBS-added DMEM, and the culture supernatant sampled from the cultured product of the three-dimensional skin model was added to this cultured product. One day after addition, the cells were collected and the mRNA was extracted with Trizol. The cDNA was rapidly prepared, and the aforementioned primers were used for real-time PCR to evaluate the gene expression levels of the gene COL5A1 for type V collagen (FIG. 14). Addition of the three-dimensional skin model culture supernatant significantly increased expression of type V collagen. This suggested that the three-dimensional skin model culture supernatant contained a factor that promotes production of type V collagen.

Example 12: Search for Factor that Promotes Type V Collagen Expression

A three-dimensional skin model (EFT-400) purchased from MatTeK was cultured in special medium (EFT400-ASY) containing added CGS27023A (final concentration: $10^{-5}$ M) and BIPBIPU (final concentration: $10^{-5}$ M). The epidermis was collected from the skin model on the 2nd day, 4th day and 7th day of culturing, and RIPA buffer by Nacalai was used to prepare a protein extract. Using a membrane array kit (ab134002) by Abcam Co., the amounts of different cytokines in the protein extract were detected using a LAS-1000UVmini by Fujifilm and digitized with the included software, and a graph was drawn (data not shown). The cytokines whose amounts increased compared to the control were selected as candidate cytokines that promote type V collagen expression. Three cytokines including PDGF-BB were selected as candidate cytokines.

The selected recombinant cytokine proteins were purchased from R&D Co. Normal human fibroblasts from skin harvested from 14-month-old children were cultured for 24 hours in 10% FBS-added DMEM, and the medium in the cultured product was exchanged with another medium added to DMEM medium containing 25% serum for a prescribed concentration of each cytokine, after which culturing was continued for 24 hours. After culturing, the cells were collected and the mRNA was extracted with Trizol. The cDNA was rapidly prepared, and the aforementioned primers were used for real-time PCR to evaluate the gene expression levels of the gene COL5A1 for type V collagen (FIG. 15). Of the three cytokines, only PDGF-BB significantly increased type V collagen production. This suggests that PDGF-BB is a cytokine produced from the epidermal side, and is a factor that acts on fibroblasts directly under the basal membrane to promote type V collagen expression.

Example 13: Sites of PDGF-BB Action and Changes in PDGF-BB Expression

A paraffin block taken in the same manner as Example 11 was used to prepare 3 μm-thick slices, and fluorescent immunostaining was performed using antibody for PDGFR-β (R&D Systems, Cat #; MAB1263) and antibody for cytokeratin 14 (K-14) (Fitzgerald, Cat #; 20R-CP002) (FIG. 16A). It is seen that PDGFR-β-expressing cells are highly abundant directly under the basal membrane, regardless of age. This confirmed that PDGF-BB secreted from the basal membrane or epidermal side can act on fibroblasts directly under the basal membrane.

Figure 16B:
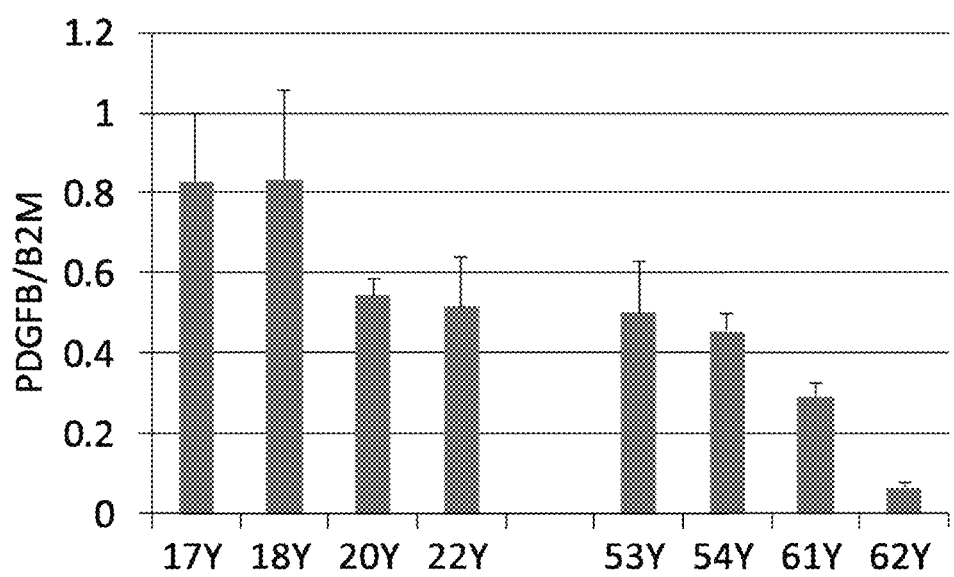
FIG. 16B is a graph showing expression levels of gene PDGFB for PDGF-BB protein, in normal human epidermis cells of different age groups.

Normal human epidermis cells of different ages purchased from KAC and Bio Predic Co. were cultured and the mRNA was extracted. The cDNA was rapidly prepared, and the following primers were used to evaluate the PDGFB gene expression levels by real-time PCR (FIG. 16B).

TABLE 7

| Primer | Sequence |
| --- | --- |
| PDGFB F | CCTGGCATGCAAGTGTGA (SEQ ID No. 33) |
| PDGFB R | CGAATGGTCACCCGAGTTT (SEQ ID No. 34) |
| B2M F | GTGGGATCGAGACATGTAAGCA (SEQ ID No. 35) |
| B2M R | CAATCCAAATGCGGCATCT (SEQ ID No. 36) |

The invention claimed is:

1. A method of promoting a laminin 511 expression comprising administering at least one extract selected from the group consisting of brown algae, red algae and green algae; or 1-(2-hydroxyethyl)-2-imidazolidinone to a subject in need of promoting a laminin 511 expression, wherein the subject is a subject in need of stabilization of epidermal basal membrane and wherein said administering stabilizes epidermal basal membrane in the subject.

2. The method of claim 1 for inhibiting reduction of the number of epidermal basal stem cells or promoting proliferation of epidermal basal stem cells, wherein the subject is a subject in need of inhibiting reduction of the number of epidermal basal stem cells or promoting proliferation of epidermal basal stem cells.

3. The method of claim 1 for improving skin barrier, elasticity, moisture and inflammation, wherein the subject is a subject in need of improving skin barrier, elasticity, moisture and inflammation.

4. The method of claim 1 for inhibiting an Il-8 expression, wherein the at least one extract is at least one extract selected from the group consisting of brown algae, red algae and green algae.

* * * * *